United States Patent [19]

Shida et al.

[11] Patent Number: 4,897,106
[45] Date of Patent: Jan. 30, 1990

[54] DERIVATIVE OF 4,5-DIHYDRO-1H-1,2,4-TRIAZOLE-3-CARBOXAMIDE, AND HERBICIDAL COMPOSITION CONTAINING THE DERIVATIVE

[75] Inventors: Takafumi Shida; Yoshikazu Kubota; Isao Ichinose; Shiro Yamazaki; Hiroyasu Shinkawa, all of Iwaki, Japan

[73] Assignee: Kureha Kagaku Kogyo Kabushiki Kaisha, Tokyo, Japan

[21] Appl. No.: 42,165

[22] Filed: Apr. 24, 1987

[30] Foreign Application Priority Data

Mar. 18, 1987 [JP] Japan ................................. 62-63443
Mar. 18, 1987 [JP] Japan ................................. 62-63444
Mar. 18, 1987 [JP] Japan ................................. 62-63445
Mar. 18, 1987 [JP] Japan ................................. 62-63446

[51] Int. Cl.$^4$ .................. A01N 43/653; C07D 249/10
[52] U.S. Cl. .......................................... 71/92; 548/262
[58] Field of Search ............................ 548/262; 71/92

[56] References Cited

U.S. PATENT DOCUMENTS 4,492,597 1/1985 Aoki et al. ........................ 548/262
4,639,266 1/1987 Huebach et al. ..................... 71/92

FOREIGN PATENT DOCUMENTS 0128530 11/1984 European Pat. Off. .
0189300 7/1986 European Pat. Off. .
2017762 11/1971 Fed. Rep. of Germany .
2526271 11/1987 France .
61-171475 8/1986 Japan ................................. 548/262
61-210075 9/1986 Japan ................................. 548/262
2120665 12/1985 United Kingdom ................. 548/262

OTHER PUBLICATIONS

Farmaco Edizione Scientifica, vol. 40, p. 272 (1985).

Primary Examiner—Richard L. Raymond
Assistant Examiner—Patricia L. Morris
Attorney, Agent, or Firm—John P. White

[57] ABSTRACT

Disclosed herein are a derivative of 4,5-dihydro-1H-1,2,4-triazole-3-carboxamide represented by the formula (Io):

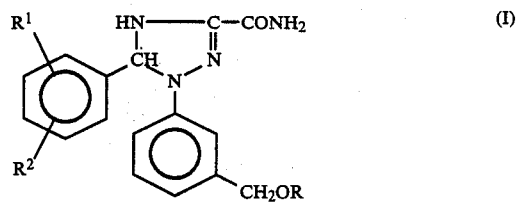

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s), an intermediate for producing the derivative and a herbicidal composition containing the derivative as an active ingredient.

25 Claims, No Drawings

DERIVATIVE OF 4,5-DIHYDRO-1H-1,2,4-TRIAZOLE-3-CARBOXAMIDE, AND HERBICIDAL COMPOSITION CONTAINING THE DERIVATIVE

BACKGROUND OF THE INVENTION

The present invention relates to a derivative of 4,5-dihydro-1H-1,2,4-triazole-3-carboxamide utilized as an active ingredient of a herbicide, an intermediate for producing the derivative and a herbicidal composition containing the derivative as an active ingredient.

Rice plant, wheat and corn are the important crop plants, and the use of a herbicide is indispensable for protecting these crop plants from the damage by weeds and for yielding a good harvest of crops.

Hitherto, there have been few reports on the derivatives of 4,5-dihydro-1H-1,2,4-triazole-3-carboxamide, and only a few compounds have been disclosed in Japanese Patent Applications Laying-Open (KOKAI) No. 61-171475(1986) and No. 61-210075(1986) such as those represented by the formula (I'):

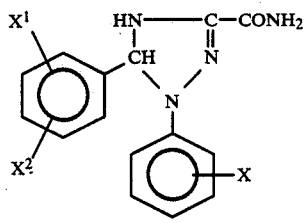

wherein X represents a hydrogen atom, a 3-methyl group or a 4-chlorine atom, $X^1$ represents a hydrogen atom and $X^2$ represents a hydrogen atom, a 4-chlorine atom, a 4-hydroxy group, a 2-hydroxy group, a 2-carboxyl group, a 3-methyl group or a 3-hydroxy group.

Although in Japanese Patent Application Laying-Open (KOKAI) No. 61-210075 (1986), it is described that the compound represented by the formula (I') has a herbicidal activity, the herbicidal effect of the compound is not satisfactory and also the selectivity of the compound cannot be said to be excellent, therefore, the development of a compound which shows an excellent selective herbicidal activity only to weeds without damaging the useful crop plants such as rice plant, wheat, corn, etc. has been strongly demanded.

As a result of the present inventors' studies for developing a compound which shows an excellent herbicidal activity without damaging the useful crop plants such as rice plant, wheat, corn, etc., it has been found out by the present inventors that a derivative of 4,5-dihydro-1H-1,2,4-triazole-3-carboxamide represented by the formula (I):

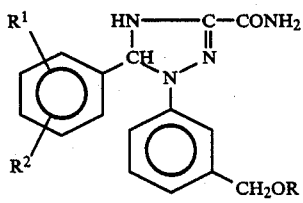

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s), has an excellent selective herbicidal activity and further that a derivative of methyl chlorophenylhydrazonoacetate represented by the formula (II):

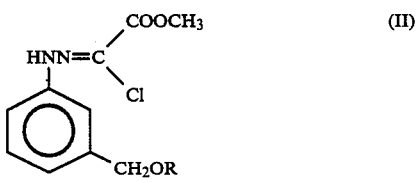

wherein R has the same meaning as above and a phenylhydrazone derivative of oxamide represented by the formula (III):

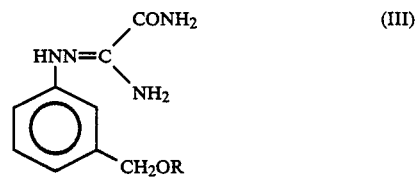

wherein R has the same meaning as above, are useful as the intermediate for producing the derivative of 4,5-dihydro-1H-1,2,4-triazole-3-carboxamide, and on the basis of the findings, the present inventors have accomplished the present invention.

SUMMARY OF THE INVENTION

In a first aspect of the invention, there is provided a derivative of 4,5-dihydro-1H-1,2,4-triazole-3-carboxamide represented by the formula (I):

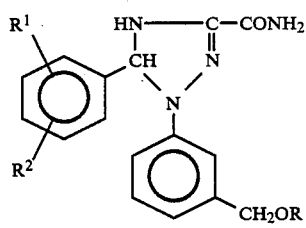

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s).

In a second aspect of the invention, there is provided a herbicidal composition comprising a herbicidally effective amount of a derivative of 4,5-dihydro-1H-1,2,4-triazole-3-carboxamide represented by the formula (I):

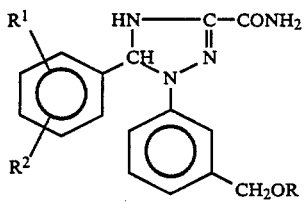

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s) and a herbicidally acceptable carrier or an adjuvant.

In a third aspect of the invention, there is provided a derivative of methyl chlorophenylhydrazonoacetate, which is represented by the formula (II):

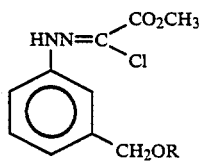

wherein R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of from 2 to 8 carbon atoms which is substituted by fluorine atom(s).

In a fourth aspect of the invention, there is provided a phenylhydrazone derivative of oxamide represented by the formula (III):

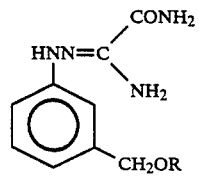

wherein R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s).

In a fifth aspect of the invention, there is provided a process for producing a derivative of methyl chlorophenylhydrazonoacetate represented by the formula (II):

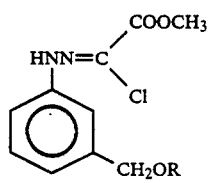

wherein R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s), which process comprises (1) subjecting 3-nitrobenzyl chloride to reaction with a compound represented by the formula (V):

ROH                                                         (V)

wherein R is the same as above, at a temperature of from −10° to 150° C. in the presence of an acceptor for hydrogen chloride formed, (2) reducing the thus obtained nitrobenzyl ether which is represented by the formula (VI):

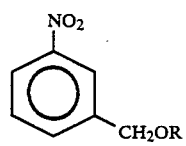

wherein R is the same as above, (3) diazotizing the thus obtained derivative of aniline, which is represented by the formula (VII):

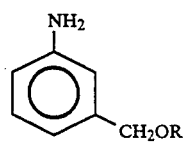

wherein R is the same as above, and (4) subjecting the thus obtained diazonium salt represented by the formula (VIII):

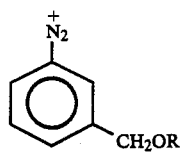
(VIII)

wherein R is the same as above, to reaction with methyl ester of 2-chloroacetoacetic acid represented by the formula (IX):

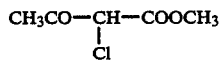
(IX)

at a temperature of from −10° to 50° C. in the presence of base.

In a sixth aspect of the invention, there is provided a process for producing a phenylhydrazone derivative of oxamide represented by the formula (III):

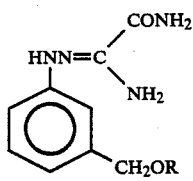
(III)

wherein R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s), which process comprises (1) subjecting 3-nitrobenzyl chloride to reaction with a compound represented by the formula (V):

ROH  (V)

wherein R is the same as above, at a temperature of from −10° to 150° C. in the presence of an acceptor for hydrogen chloride formed, (2) reducing the thus obtained nitrobenzyl ether which is represented by the formula (VI):

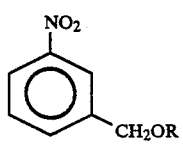
(VI)

wherein R is the same as above, (3) diazotizing the thus obtained derivative of aniline, which is represented by the formula (VII):

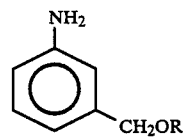
(VII)

wherein R is the same as above, (4) subjecting the thus obtained diazonium salt represented by the formula (VIII):

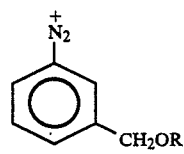
(VIII)

wherein R is the same as above, to reaction with methyl ester of chloroacetoacetic acid represented by the formula (IX):

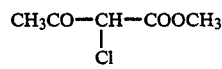
(IX)

at a temperature of from −10° to 50° C. in the presence of base, and (5) subjecting the thus obtained derivative of methyl chlorophenylhydrazonoacetate represented by the formula (II):

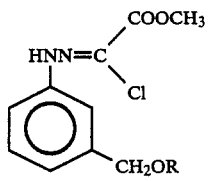
(II)

wherein R is the same as above, to reaction with ammonia in an alcohol at a temperature of from −10° to 50° C.

In a seventh aspect of the invention, there is provided a process for producing a derivative of 4,5-dihydro-1H-1,2,4-triazole-3-carboxamide represented by the formula (I):

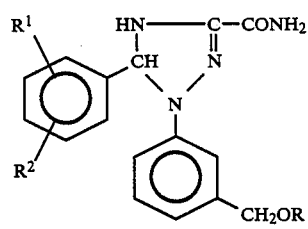
(I)

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s), which process comprises (1) subjecting 3-nitrobenzyl chloride to reaction with a compound represented by the formula (V):

ROH         (V)

wherein R is the same as above, at a temperature of from −10° to 150° C. in the presence of an acceptor for hydrogen chloride formed, (2) reducing the thus obtained nitrobenzyl ether which is represented by the formula (VI):

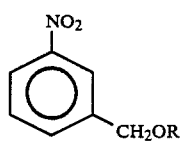
(VI)

wherein R is the same as above, (3) diazotizing the thus obtained derivative of aniline, which is represented by the formula (VII):

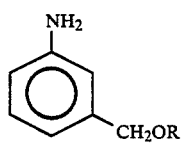
(VII)

wherein R is the same as above, and (4) subjecting the thus obtained diazonium salt represented by the formula (VIII):

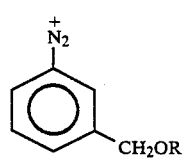
(VIII)

wherein R is the same as above, to reaction with an ester of 2-chloroacetoacetic acid represented by the formula (IX):

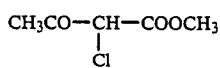
(IX)

at a temperature of from −10° to 50° C. in the presence of base, (5) subjecting the thus obtained derivative of methyl chlorophenylhydrazonoacetate represented by the formula (II):

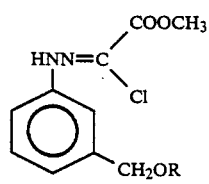
(II)

wherein R is the same as above, to reaction with ammonia in an alcohol at a temperature of from −10° C. to 50° C., and (6) subjecting the thus obtained phenylhydrazone derivative of oxamide represented by the formula (III):

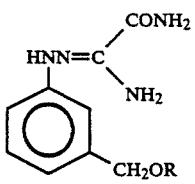
(III)

wherein R is the same as above, and a non-substituted- or substituted-benzaldehyde represented by the formula (X):

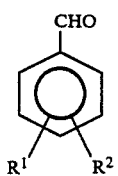
(X)

wherein $R^1$ and $R^2$ are respectively the same as above, to dehydration reaction at a temperature of from −10° to 150° C. in the presence of an acid catalyst.

DETAILED DESCRIPTION OF THE INVENTION

The derivative of 4,5-dihydro-1H1,2,4-triazole-3-carboxamide, which has an excellent selective herbicidal activity according to the present invention, is represented by the formula (I):

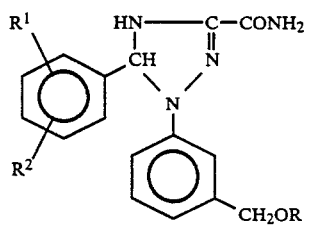
(I)

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8, preferably 3 to 6 carbon atoms, a branched-chain alkyl group of 3 to 8, preferably 3 to 6 carbon atoms, a cycloalkyl group of 3 to 8, preferably 4 to 7 carbon atoms, a (cycloalkyl)alkyl group of 4 to 8 carbon atoms, preferably an alkyl group of 1 to 3 carbon atoms having a cycloaliphatic structure of 3 to 7 carbon atoms, an alkenyl group of 3 to 8, preferably 3 to 6 carbon atoms, an alkynyl group of 3 to 8, preferably 3 to 6 carbon atoms, an alkoxyalkyl group of 3 to 8 carbon atoms, preferably an alkyl group of 2 to 4 carbon atoms having an alkoxy group of 1 to 4 carbon atoms, a phenyl group, an aralkyl group of 7 to 9 carbon atoms, a phenyl group substituted by perferably 1 to 3 halogen atoms or an alkyl group of 2 to 8, preferably 2 to 7 carbon atoms, which is substituted by preferably 1 to 15 fluorine atoms.

The derivatives of 4,5-dihydro-1H-1,2,4-triazole-3-carboxiamide represented by the formula(I) according to the present inventin and their physicochemical properties are exemplified in Table 1, and the results of elementary analysis of the derivatives are shown in Table 2.

Furthermore, the physicochemical properties and the results of elementary analysis of the compounds of the formulae (II) and (III), which are the useful intermediates for producing the derivative of 4,5-dihydro-1H-1,2,4-triazole-3-carboxamide represented by the formula(I), are shown in Tables 3 to 6 respectively.

TABLE 1

(I)

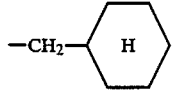

| No. | $R^1$ | $R^2$ | R | Yield of synthesis (%) | Melting point (°C.) | NMR Spectrum (CDCl$_3$, δ, ppm, 60 MHz) |
|---|---|---|---|---|---|---|
| 1 | H | H | —(CH$_2$)$_2$CH$_3$ | 81.7 | 158~159 | 0.87(3H, t, 6Hz), 1.43(2H, 6-plet, 6Hz), 3.30(2H, t, 6Hz), 4.30(2H, s), 6.30(1H, s), 6.5~7.8(12H, m)* |
| 2 | H | H | —(CH$_2$)$_3$CH$_3$ | 60.0 | 155~156 | 0.87(3H, t, 6Hz), 1.1~1.7(4H, m), 3.37(2H, t, 6Hz), 4.33(2H, s), 6.30(1H, d, 2Hz), 6.6~7.7(12H, m)* |
| 3 | H | H | —(CH$_2$)$_4$CH$_3$ | 78.1 | 146~149 | 0.87(3H, t, 6Hz), 1.1~1.9(6H, m), 3.30(2H, t, 6Hz), 4.27(2H, s), 6.33(1H, s), 6.6~7.6(12H, m)** |
| 4 | H | H | —(CH$_2$)$_2$CH(CH$_3$)$_2$ | 84.4 | 144~146 | 0.90(6H, d, 6Hz), 1.0~2.2(3H, m), 3.40(2H, t, 6.5Hz), 4.36(2H, s), 6.33(1H, s), 6.6~7.3(10H, m), 5.7(2H, bs) |
| 5 | H | H | —CH$_2$C(CH$_3$)$_3$ | 87.1 | 125~127 | 0.87(9H, s), 3.00(2H, s), 4.33(2H, s), 6.40(1H, d, 2Hz), 6.6~7.8(12H, m)** |
| 6 | H | H | —(CH$_2$)$_5$CH$_3$ | 80.7 | 146~148 | 0.87(3H, t, 6Hz), 1.1~1.9(8H, m), 3.33(2H, t, 6Hz), 4.30(2H, s), 6.40(1H, d, 2Hz), 6.5~7.7(12H, m)** |
| 7 | H | H | 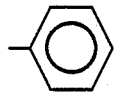 | 95.2 | 165~167 | 0.8~1.0(2H, m), 1.11~1.3(3H, m), 1.5~1.8(6H, m), 3.18(2H, d, 6.4Hz), 4.39(2H, s), 5.39(2H, bs), 6.40(1H, d, 1.95Hz), 6.65(1H, bs), 6.77(2H, m), 6.93(1H, bs), 7.13(1H, t, 7.8Hz), 7.3~7.5(5H, m)*** |
| 8 | H | H | —CH$_2$CH=CH$_2$ | 95.8 | 147~148 | 3.94(2H, dt, 5.4, 1.5Hz), 4.43(2H, s), 5.17(1H, dq, 10.7, 1.5Hz), 5.24(1H, dq, 17.1, 1.5Hz), 5.90(1H, ddt, 17.1, 10.7, 5.4Hz), 6.40(1H, s), 6.72(1H, dd, 7.8, 1.5Hz), 6.80(1H, d, 7.8Hz), 6.99(1H, s), 7.13(1H, t, 7.8Hz), 7.27~7.5(5H, m), 5.41(2H, bs), 6.65(1H, bs)*** |
| 9 | H | H | —(CH$_2$)$_2$O(CH$_2$)$_3$CH$_3$ | 86.5 | 126~128 | 0.91(3H, t, 7.1Hz), 1.36(2H, 6-plet, 7.1Hz), 1.57(2H, tt, 7.1, 6.6Hz), 3.44(2H, t, 6.6Hz), 3.53(4H, s), 4.48(2H, s), 5.39(2H, bs), 6.40(1H, s), 6.60(1H, bs), 6.71(1H, dd, 7.8, 1.5Hz), 6.80(1H, d, 7.8Hz), 6.99(1H, bs), 7.12(1H, t, 7.8Hz), 7.3~7.5(5H, m)*** |
| 10 | H | H | 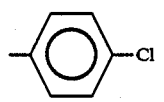 | 85.5 | 177~178 | 4.90(2H, s), 6.23(1H, s), 6.4~7.5 (17H, m)* |
| 11 | H | H | 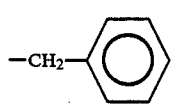—Cl | 96.3 | 214~215 | 4.93(2H, s), 6.27(1H, d, 2Hz), 6.86(2H, d, 8Hz), 7.20(2H, d, 8Hz), 6.7~7.7 (12H, m)* |
| 12 | H | H | —CH$_2$— (phenyl) | 87.6 | 162~163 | 4.40(2H, s), 4.43(2H, s), 6.6~7.6 (18H, m)** |
| 13 | H | H | —CH$_2$CF$_3$ | 92.9 | 180~181 | 3.67(2H, q, 8Hz), 4.57(2H, s), 6.40(1H, |

TABLE 1-continued $$\text{(I)}$$

Structure: diagram of compound (I) with substituents $R^1$, $R^2$ on one phenyl ring, and $CH_2OR$ on another phenyl ring, connected via CH–N–N=C(CONH$_2$)–NH.

| No. | $R^1$ | $R^2$ | R | Yield of synthesis (%) | Melting point (°C.) | NMR Spectrum (CDCl$_3$, δ, ppm, 60 MHz) |
|---|---|---|---|---|---|---|
| 14 | H | H | —CH$_2$CF$_2$CHF$_2$ | 91.0 | 160~161 | s), 6.6~7.6(12H, m)* 3.67(2H, tt, 12.5Hz), 4.47(2H, s), 5.90(1H, tt, 54, 5Hz), 6.33(1H, s), 6.6~7.6(12H, m)* |
| 15 | H | H | —CH$_2$CF$_2$CF$_3$ | 92.7 | 146~148 | 3.73(2H, tt, 13, 2Hz), 4.53(2H, s), 5.6(2H, bs), 6.34(1H, s), 6.7~7.7 (10H, m) |
| 16 | H | H | —CH$_2$CF$_2$CHFCF$_3$ | 84.1 | 129~131 | 3.3~4.0(2H, m), 4.40(2H, s), 5.03(1H, d, 6-plet, 50, 60Hz), 6.20(1H, s), 6.5~7.5(12H, m) |
| 17 | H | H | —CH$_2$(CF$_2$)$_2$CF$_3$ | 91.0 | 128~130 | 3.80(2H, tt, 13.5, 1.5Hz), 4.56(2H, s), 5.70(1H, s), 5.8(2H, bs), 6.36(1H, d, 2Hz), 6.7~7.6(9H, m) |
| 18 | H | H | —CH$_2$(CF$_2$)$_3$CHF$_2$ | 86.9 | 120~122 | 3.87(2H, tt, 14, 1.5Hz), 4.50(2H, s), 6.37(1H, s), 6.40(1H, tt, 52, 5.5Hz), 6.5~7.6(12H, m)** |
| 19 | H | H | —CH$_2$(CF$_2$)$_5$CHF$_2$ | 70.5 | 132~134 | 3.87(2H, t, 14Hz), 4.50(2H, s), 6.50(1H, tt, 50, 5Hz), 6.33(1H, s), 6.5~7.7(12H, m)** |
| 20 | 2-F | H | —(CH$_2$)$_3$CH$_3$ | 89.8 | 128~130 | 0.90(3H, t, 6Hz), 1.1~1.6(4H, m), 3.40(2H, t, 6Hz), 4.37(2H, s), 6.73 (1H, d, 2Hz), 6.6~7.6(11H, m)* |
| 21 | 2-F | H | —(CH$_2$)$_4$CH$_3$ | 62.4 | 120~121 | 0.87(3H, t, 6Hz), 1.0~1.91(6H, m), 3.33(2H, t, 6Hz), 4.33(2H, s), 6.5~7.6(12H, m)** |
| 22 | 2-F | H | —(CH$_2$)$_2$CH(CH$_3$)$_2$ | 78.9 | 120~122 | 0.90(6H, d, 6Hz), 1.0~2.2(4H, m), 3.40(2H, t, 6.5Hz), 4.37(2H, s), 5.8(2H, bs), 6.5~7.6(10H, m) |
| 23 | 3-F | H | —(CH$_2$)$_2$CH(CH$_3$)$_2$ | 83.1 | 129~130 | 0.90(6H, d, 6Hz), 1.0~2.0(4H, m), 3.37(2H, t, 6.5Hz), 4.37(2H, s), 5.8(2H, bs), 6.30(1H, s), 6.5~7.7 (9H, m) |
| 24 | 4-F | H | —(CH$_2$)$_2$CH(CH$_3$)$_2$ | 87.3 | 136~138 | 0.90(6H, d, 6Hz), 1.2~2.0(4H, m), 3.37(2H, t, 6.5Hz), 4.33(2H, s), 5.7(2H, bs), 6.27(1H, s), 6.5~7.5 (9H, m) |
| 25 | 2-F | H | —CH$_2$C(CH$_3$)$_3$ | 75.4 | 119~120 | 0.87(9H, s), 3.03(2H, s), 4.40(2H, s), 6.5~7.5(12H, m)** |
| 26 | 2-F | H | —(CH$_2$)$_5$CH$_3$ | 82.4 | 134~135 | 0.87(3H, t, 6Hz), 1.1~1.9(8H, m), 3.30(2H, t, 6Hz), 4.30(2H, s), 6.5~7.6(12H, m)** |
| 27 | 2-F | H | —CH$_2$-cyclohexyl | 95.8 | 148~149 | 0.8~1.0(2H, m), 1.0~1.3(3H, m), 1.5~1.8(6H, m), 3.20(2H, d, 6.4Hz), 4.41(2H, s), 6.77(1H, d, 1.5Hz), 6.79(1H, d, 7.8Hz), 6.81(1H, d, 7.8Hz), 6.98(1H, s), 7.71(1H, t, 7.8Hz), 7.07~7.15(2H, m), 7.28~7.40(2H, m), 5.41(1H, bs), 5.51(1H, s), 6.64(1H, bs)*** |
| 28 | 2-F | H | —phenyl | 86.7 | 176~178 | 4.90(2H, s), 6.63(1H, s), 6.6~7.5 (16H, m)* |
| 29 | 2-F | H | —(4-Cl-phenyl) | 88.7 | 206~207 | 4.90(2H, s), 6.60(1H, d, 2Hz), 6.86 (2H, d, 8Hz), 7.20(2H, d, 8Hz), 6.6~7.7(11H, m)* |
| 30 | 2-F | H | —CH$_2$CH=CH$_2$ | 79.7 | 133~135 | 3.97(2H, dt, 5.4, 1.5Hz), 4.45(2H, s), 5.17(1H, dq, 10.3, 1.5Hz), 5.25(1H, dq, 17.1, 1.5Hz), 5.91(1H, ddt, 17.1, 10.3, 1.5Hz), 6.74(1H, dd, 7.8, 1.5Hz), 6.77(1H, d, 1.5Hz), 6.83(1H, d, 7.8Hz), |

TABLE 1-continued

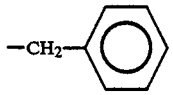

| No. | R¹ | R² | R | Yield of synthesis (%) | Melting point (°C.) | NMR Spectrum (CDCl₃, δ, ppm, 60 MHz) |
|---|---|---|---|---|---|---|
| | | | | | | 7.00(1H, s), 7.16(1H, t, 7.8Hz), 7.05~7.25(2H, m), 7.27~7.5(2H, m)*** 5.42(1H, bs), 5.52(1H, bs), 6.65(1H, bs)*** |
| 31 | 2-F | H | —CH₂CF₃ | 90.2 | 175~176 | 3.73(2H, q, 8Hz), 4.53(2H, s), 6.6~7.6(12H, m) |
| 32 | 2-F | H | —CH₂CF₂CHF₂ | 84.4 | 159~160 | 3.70(2H, tt, 12.5, 1.5Hz), 4.47(2H, s), 5.97(1H, tt, 54, 5Hz), 6.6~7.7(12H, m)* |
| 33 | 2-F | H | —CH₂CF₂CF₃ | 80.7 | 151~153 | 3.80(2H, tq, 13, 2Hz), 4.53(2H, s), 6.70(1H, s), 6.6~7.7(11H, m)* |
| 34 | 3-F | H | —CH₂CF₂CF₃ | 83.8 | 152~154 | 3.76(2H, tq, 13, 2Hz), 4.50(2H, s), 6.30(1H, s), 6.6~7.6(11H, m)* |
| 35 | 4-F | H | —CH₂CF₂CF₃ | 64.6 | 165~167 | 3.80(2H, tq, 13, 2Hz), 4.47(2H, s), 6.27(1H, s), 6.6~7.5(11H, m)* |
| 36 | 2-F | H | —CH₂CF₂CHFCF₃ | 89.6 | 140~141 | 3.5~4.0(2H, m), 4.50(2H, s), 5.17 (1H, d, 6-plet, 50, 6Hz), 6.6~7.6 (12H, m)* |
| 37 | 2-F | H | —CH₂(CF₂)₂CF₃ | 80.9 | 136~137 | 3.80(2H, tt, 13.5, 1.5Hz), 4.53(2H, s), 5.73(2H, bs), 6.10(1H, d, 2Hz), 6.6~7.5(9H, m) |
| 38 | 3-F | H | —CH₂(CF₂)₂CF₃ | 78.0 | 125~127 | 3.80(2H, tt, 13.5, 1.5Hz), 4.46(2H, s), 6.26(1H, d, 2Hz), 6.5~7.4(11H, m)* |
| 39 | 4-F | H | —CH₂(CF₂)₂CF₃ | 88.3 | 133~136 | 3.83(2H, tt, 13.5, 1.5Hz), 4.53(2H, s), 6.33(1H, d, 2Hz), 6.6~7.6(11H, m)* |
| 40 | 2-F | H | —CH₂(CF₂)₃CHF₂ | 69.3 | 128~130 | 3.87(2H, tt, 14, 2Hz), 4.50(2H, s), 6.37(1H, tt, 52, 6Hz), 6.5~7.6(12H, m) |
| 41 | 4-CH₃ | H | —(CH₂)₂CH(CH₃)₂ | 80.4 | 135~136 | 0.92(6H, d, 6Hz), 1.1~2.1(3H, m), 2.33 (3H, s), 3.40(2H, t, 6.5Hz), 4.37(2H, s), 5.6(2H, bs), 6.32(1H, s), 6.6~7.5(9H, m) |
| 42 | 4-CH₃ | H | —CH₂(CF₂)₂CF₃ | 79.9 | 130~132 | 2.30(3H, s), 2.83(2H, tt, 13.5, 1.5Hz), 4.50(2H, s), 6.30(1H, s), 7.12(2H, d, 8Hz), 7.34(2H, d, 8Hz), 6.6~7.4 (7H, m)* |
| 43 | 4-Cl | H | —(CH₂)₂CH(CH₃)₂ | 88.7 | 143~145 | 0.87(6H, d, 6Hz), 1.2~2.0(3H, m), 3.38(2H, t, 6.5Hz), 4.37(2H, s), 5.67(2H, bs), 6.30(1H, d, 2Hz), 6.5~7.4(9H, m) |
| 44 | 4-Cl | H | —CH₂CF₂CF₃ | 95.6 | 168~170 | 3.83(2H, tq, 13, 2Hz), 4.53(2H, s), 6.30(1H, d, 2Hz), 6.5~7.5(11H, m)* |
| 45 | 4-Cl | H | —CH₂(CF₂)₂CF₃ | 82.7 | 145~148 | 3.83(2H, tt, 13.5, 1.5Hz), 4.53(2H, s), 6.30(1H, d, 2Hz), 6.6~7.5(11H, m)* |
| 46 | 4-OCH₃ | H | —(CH₂)₂CH(CH₃)₂ | 84.5 | 150~151 | 0.87(6H, d, 6Hz), 1.2~2.1(3H, m), 3.38(2H, t, 6.5Hz), 3.72(3H, s), 4.37(2H, s), 5.63(2H, bs), 6.27(1H, s), 6.82(2H, d, 8Hz), 7.28(2H, d, 8Hz), 6.5~7.2(5H, m) |
| 47 | 4-OCH₃ | H | —CH₂(CF₂)₂CF₃ | 75.2 | 110~113 | 3.73(3H, s), 3.80(2H, tt, 13.5, 1.5Hz), 4.50(2H, s), 6.27(1H, d, 2Hz), 6.84(2H, d, 8Hz), 7.36(2H, d, 8Hz), 6.6~7.6(7H, m)* |
| 48 | 2-F | H | —CH₂—⌬ | 80.7 | 162~163 | 4.40(2H, s), 4.43(2H, s), 6.6~7.6 (17H, m)** |
| 49 | 2-F | H | —(CH₂)₂O(CH₂)₃CH₃ | 94.9 | 112~113 | 0.91(3H, t, 7.1Hz), 1.36(2H, 6-plet, 7.1Hz), 1.57(2H, tt, 7.1, 6.8Hz), 3.45(2H, t, 6.8Hz), 3.55(4H, s), 4.49(2H, s), 6.71(1H, dd, 7.8, 1.5Hz), 6.76(1H, d, 2Hz), 6.83(1H, d, 7.8Hz), 7.01(1H, s), 7.15(1H, t, 7.8Hz), 7.05~7.25(2H, m), 7.27~7.45(2H, |

TABLE 1-continued

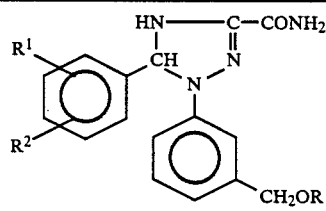

(I)

| No. | R¹ | R² | R | Yield of synthesis (%) | Melting point (°C.) | NMR Spectrum (CDCl₃, δ, ppm, 60 MHz) |
|---|---|---|---|---|---|---|
| | | | | | | m), 5.43(1H, bs), 5.52(1H, s), 6.67(1H, bs)*** |
| 50 | 2-F | H | —CH₂(CF₂)₅CHF₂ | 87.7 | 128~129 | 3.77(2H, t, 14Hz), 4.43(2H, s), 6.20(1H, tt, 50, 5Hz), 6.5~7.5 (12H, m)* |
| 51 | 2-F | H | —(CH₂)₂CH₃ | 92.6 | 149~150 | 0.87(3H, t, 6Hz), 1.57(2H, 6-plet, 6Hz), 3.33(2H, t, 6Hz), 4.47(2H, s), 5.80(1H, bd, 2Hz), 6.0(1H, bs), 6.6~7.5(10H, m) |
| 52 | 4-CH₃ | H | —CH₂CF₂CF₃ | 85.9 | 132~134 | 2.30(3H, s), 3.80(2H, tq, 13, 2Hz), 4.50(2H, s), 6.30(1H, s), 6.6~7.5 (11H, m)* |
| 53 | 2-F | 6-F | —CH₂CF₂CF₃ | 86.2 | 180~182 | 3.80(2H, tq, 13, 2Hz), 4.47(2H, s), 6.5~7.4(11H, m) |

Notes:
*determined in a mixed solvent of CDCl₃ + DMSO—d₆
**determined in a mixed solvent of CDCl₃ + acetone—d₆ and
***determined in an apparatus of 250 MHz.

TABLE 2

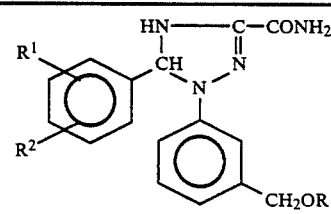

(I)

| No. | Molecular formula | C (%) Found/Calculated | H (%) Found/Calculated | N(%) Found/Calculated |
|---|---|---|---|---|
| 1 | C₁₉H₂₂N₄O₂ | 67.61 / 67.44 | 6.64 / 6.55 | 16.72 / 16.56 |
| 2 | C₂₀H₂₄N₄O₂ | 68.18 / 68.16 | 6.77 / 6.86 | 16.09 / 15.90 |
| 3 | C₂₁H₂₆N₄O₂ | 68.77 / 68.83 | 7.29 / 7.15 | 15.46 / 15.29 |
| 4 | C₂₁H₂₆N₄O₂ | 68.63 / 68.83 | 6.98 / 7.15 | 15.17 / 15.29 |
| 5 | C₂₁H₂₆N₄O₂ | 68.65 / 68.83 | 7.09 / 7.15 | 15.09 / 15.29 |
| 6 | C₂₂H₂₈N₄O₂ | 69.41 / 69.45 | 7.23 / 7.42 | 14.80 / 14.72 |
| 7 | C₂₃H₂₈N₄O₂ | 70.41 / 70.38 | 7.26 / 7.19 | 14.08 / 14.27 |
| 8 | C₁₉H₂₀N₄O₂ | 67.81 / 67.84 | 5.95 / 5.99 | 16.65 / 16.65 |
| 9 | C₂₂H₂₈N₄O₃ | 66.73 / 66.65 | 7.29 / 7.12 | 14.14 / 14.13 |
| 10 | C₂₂H₂₀N₄O₂ | 70.86 / 70.95 | 5.28 / 5.41 | 14.97 / 15.04 |
| 11 | C₂₂H₁₉ClN₄O₂ | 65.10 / 64.95 | 4.72 / 4.71 | 13.67 / 13.77 |
| 12 | C₂₃H₂₂N₄O₂ | 71.29 / 71.48 | 5.89 / 5.74 | 14.59 / 14.50 |
| 13 | C₁₈H₁₇F₃N₄O₂ | 57.08 / 57.14 | 4.72 / 4.53 | 14.73 / 14.81 |
| 14 | C₁₉H₁₈F₄N₄O₂ | 55.60 / 55.61 | 4.47 / 4.42 | 13.45 / 13.65 |
| 15 | C₁₉H₁₇F₅N₄O₂ | 53.08 / 53.28 | 4.15 / 4.00 | 12.90 / 13.08 |
| 16 | C₂₀H₁₈F₆N₄O₂ | 52.24 / 52.18 | 4.14 / 3.94 | 12.32 / 12.17 |
| 17 | C₂₀H₁₇F₇N₄O₂ | 50.12 / 50.22 | 3.39 / 3.58 | 11.56 / 11.71 |
| 18 | C₂₁H₁₈F₈N₄O₂ | 49.25 / 49.42 | 3.39 / 3.55 | 11.01 / 10.98 |
| 19 | C₂₃H₁₈F₁₂N₄O₂ | 45.30 / 45.26 | 2.77 / 2.97 | 9.05 / 9.18 |
| 20 | C₂₀H₂₃FN₄O₂ | 65.04 / 64.85 | 6.21 / 6.26 | 15.21 / 15.12 |
| 21 | C₂₁H₂₅FN₄O₂ | 65.71 / 65.61 | 6.64 / 6.55 | 14.76 / 14.57 |
| 22 | C₂₁H₂₅FN₄O₂ | 64.45 / 65.61 | 6.75 / 6.55 | 14.47 / 14.57 |
| 23 | C₂₁H₂₅FN₄O₂ | 65.69 / 65.61 | 6.37 / 6.55 | 14.70 / 14.57 |
| 24 | C₂₁H₂₅FN₄O₂ | 65.72 / 65.61 | 6.74 / 6.55 | 14.77 / 14.57 |
| 25 | C₂₁H₂₅FN₄O₂ | 65.41 / 65.61 | 6.73 / 6.55 | 14.77 / 14.57 |
| 26 | C₂₂H₂₇FN₄O₂ | 66.26 / 66.31 | 6.68 / 6.83 | 14.20 / 14.06 |
| 27 | C₂₃H₂₇FN₄O₂ | 67.43 / 67.30 | 6.57 / 6.63 | 13.45 / 13.65 |
| 28 | C₂₂H₁₉FN₄O₂ | 67.49 / 67.68 | 4.72 / 4.91 | 14.18 / 14.35 |
| 29 | C₂₂H₁₈FClN₄O₂ | 62.18 / 62.20 | 4.08 / 4.27 | 13.17 / 13.19 |
| 30 | C₁₉H₁₉FN₄O₂ | 64.41 / 64.40 | 5.29 / 5.40 | 15.98 / 15.81 |
| 31 | C₁₈H₁₆F₄N₄O₂ | 54.37 / 54.55 | 4.10 / 4.07 | 14.14 / 14.14 |
| 32 | C₁₉H₁₇F₅N₄O₂ | 53.08 / 53.28 | 4.15 / 4.00 | 12.90 / 13.08 |
| 33 | C₁₉H₁₆F₆N₄O₂ | 51.27 / 51.13 | 3.41 / 3.61 | 12.52 / 12.55 |

TABLE 2-continued

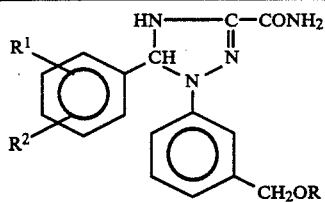 (I)

| No. | Molecular formula | C (%) Found/Calculated | H (%) Found/Calculated | N (%) Found/Calculated |
|---|---|---|---|---|
| 34 | $C_{19}H_{16}F_6N_4O_2$ | 50.93 / 51.13 | 3.61 / 3.61 | 12.49 / 12.55 |
| 35 | $C_{19}H_{16}F_6N_4O_2$ | 51.11 / 51.13 | 3.79 / 3.61 | 12.52 / 12.55 |
| 36 | $C_{20}H_{17}F_7N_4O_2$ | 50.12 / 50.22 | 3.39 / 3.58 | 11.56 / 11.71 |
| 37 | $C_{20}H_{16}F_8N_4O_2$ | 48.43 / 48.40 | 3.43 / 3.25 | 11.24 / 11.29 |
| 38 | $C_{20}H_{16}F_8N_4O_2$ | 48.46 / 48.40 | 3.42 / 3.25 | 11.20 / 11.29 |
| 39 | $C_{20}H_{16}F_8N_4O_2$ | 48.20 / 48.40 | 3.06 / 3.25 | 11.09 / 11.29 |
| 40 | $C_{21}H_{17}F_9N_4O_2$ | 47.71 / 47.74 | 3.41 / 3.24 | 10.46 / 10.60 |
| 41 | $C_{22}H_{28}N_4O_2$ | 69.63 / 69.45 | 7.52 / 7.42 | 14.80 / 14.72 |
| 42 | $C_{21}H_{19}F_7N_4O_2$ | 51.19 / 51.23 | 4.08 / 3.89 | 11.50 / 11.38 |
| 43 | $C_{21}H_{25}ClN_4O_2$ | 63.01 / 62.92 | 6.29 / 6.29 | 14.14 / 13.97 |

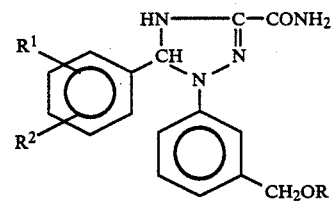 (I)

| No. | Molecular formula | C (%) Found/Calculated | H (%) Found/Calculated | N (%) Found/Calculated |
|---|---|---|---|---|
| 44 | $C_{19}H_{16}F_5ClN_4O_2$ | 49.34 / 49.31 | 3.43 / 3.48 | 12.30 / 12.11 |
| 45 | $C_{20}H_{16}F_7ClN_4O_2$ | 46.78 / 46.84 | 3.15 / 3.14 | 11.05 / 10.93 |
| 46 | $C_{22}H_{28}N_4O_3$ | 66.45 / 66.65 | 7.26 / 7.12 | 14.11 / 14.13 |
| 47 | $C_{21}H_{19}F_7N_4O_3$ | 49.53 / 49.61 | 3.76 / 3.77 | 14.11 / 11.02 |
| 48 | $C_{23}H_{21}FN_4O_2$ | 68.11 / 68.31 | 5.41 / 5.23 | 13.91 / 13.85 |
| 49 | $C_{22}H_{27}FN_4O_3$ | 63.79 / 63.75 | 6.63 / 6.57 | 13.50 / 13.52 |
| 50 | $C_{23}H_{17}F_{13}N_4O_2$ | 43.92 / 43.96 | 2.90 / 2.73 | 9.10 / 8.92 |
| 51 | $C_{19}H_{21}FN_4O_2$ | 63.93 / 64.03 | 6.00 / 5.94 | 15.74 / 15.72 |
| 52 | $C_{20}H_{19}F_5N_4O_2$ | 54.39 / 54.30 | 4.20 / 4.33 | 12.83 / 12.66 |
| 53 | $C_{19}H_{15}F_7N_4O_2$ | 49.34 / 49.15 | 3.44 / 3.26 | 12.26 / 12.07 |

TABLE 3

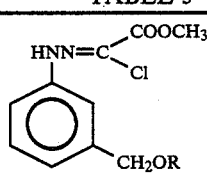 (II)

| No. | R | Yield of synthesis (%) | Melting point (°C.) | NMR Spectrum (CDCl$_3$, δ, ppm, 60 MHz) |
|---|---|---|---|---|
| 1' | $CH_3(CH_2)_2-$ | 75.5 | Oil | 0.93(3H, t, 7Hz), 1.67(2H, 6-plet, 7Hz), 3.40(2H, t, 7Hz), 3.87(3H, s), 4.45(2H, s), 6.8~7.4(4H, m), 8.37(1H, bs) |
| 2' | $CH_3(CH_2)_3-$ | 98.2 | Oil | 0.90(3H, t, 6Hz), 1.1~1.9(4H, m), 3.47(2H, t, 6Hz), 3.88(3H, s), 4.45(2H, s), 6.8~7.4 (4H, m), 8.37(1H, bs) |
| 3' | $CH_3(CH_2)_4-$ | 96.6 | Oil | 0.90(3H, t, 6Hz), 1.3~1.6(6H, m), 3.47(2H, t, 6Hz), 3.90(3H, s), 4.47(2H, s), 6.8~7.6 (4H, m), 8.37(1H, bs) |
| 4' | $(CH_3)_2CH(CH_2)_2-$ | 93.8 | Oil | 0.90(6H, d, 6Hz), 1.2~2.1(3H, m), 3.47(2H, t, 6Hz), 3.87(3H, s), 4.43(2H, s), 6.8~7.4 (4H, m), 8.40(1H, bs) |
| 5' | $(CH_3)_3CCH_2-$ | 74.3 | 67~69 | 0.93(9H, s), 3.10(2H, s), 3.90(3H, s), 4.50 (2H, s), 6.8~7.8(4H, m), 8.35(1H, bs) |
| 6' | $CH_3(CH_2)_5-$ | 90.2 | Oil | 0.87(3H, t, 6Hz), 1.1~2.1(8H, m), 3.45(2H, t, 6Hz), 3.90(3H, s), 4.47(2H, s), 6.8~7.5 (4H, m), 8.37(1H, bs) |
| 7' | phenyl | 91.2 | 115~117 | 3.90(3H, s), 5.03(2H, s), 6.8~7.7(9H, m), 8.43(1H, bs) |
| 8' | 4-chlorophenyl | 87.8 | 127~129 | 3.90(3H, s), 5.00(2H, s), 6.8~7.6(8H, m), 8.43(1H, bs) |

TABLE 3-continued (II) structure: HNN=C(COOCH₃)(Cl) attached to phenyl ring with CH₂OR substituent

| No. | R | Yield of synthesis (%) | Melting point (°C.) | NMR Spectrum (CDCl₃, δ, ppm, 60 MHz) |
|---|---|---|---|---|
| 9' | 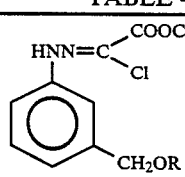 PhCH₂— | 80.1 | 86~88 | 3.90(3H, s), 4.53(4H, s), 6.9~7.6(9H, m), 8.37(1H, bs) |
| 10' | CF₃CH₂— | 80.8 | 81~83 | 3.83(2H, q, 9Hz), 3.90(3H, s), 4.63(2H, s), 6.9~7.7(4H, m), 8.43(1H, bs) |
| 11' | CHF₂CF₂CH₂— | 85.7 | Oil | 3.83(2H, tt, 12.5, 2Hz), 3.92(3H, s), 4.60 (2H, s), 5.93(1H, tt, 53, 5Hz), 6.7~7.5(4H, m), 8.40(1H, bs) |
| 12' | C₃CF₂CH₂— | 86.8 | 55~58 | 3.88(2H, tt, 13, 2Hz), 3.90(3H, s), 4.62(2H, s), 6.9~7.5(4H, m), 8.40(1H, bs) |
| 13' | CF₃CHFCF₂CH₂— | 82.5 | 67~69 | 3.6~4.2(2H, m), 3.92(3H, s), 4.63(2H, s), 5.02(1H, d, 6-plet, 50, 6Hz), 6.9~7.6(4H, m), 8.40(1H, bs) |
| 14' | CF₃(CF₂)₂CH₂— | 97.5 | Oil | 3.87(2H, tt, 13.5, 2Hz), 3.90(3H, s), 4.67(2H, s), 6.8~7.5(4H, m), 8.37(1H, bs) |
| 15' | CHF₂(CF₂)₃CH₂— | 86.3 | 53~55 | 3.90(3H, s), 3.93(2H, tt, 14, 2Hz), 4.63(2H, s), 6.03(1H, tt, 52, 5Hz), 6.8~7.5(4H, m), 8.40(1H, bs) |
| 16' | CHF₂(CF₂)₅CH₂— | 87.7 | Oil | 3.86(3H, s), 3.90(2H, t, 13.5Hz), 4.63(2H, s), 6.02(1H, tt, 52, 5Hz), 6.8~7.5(4H, m), 8.38(1H, bs) |

TABLE 4

(II) structure shown

| No. | Molecular formula | C (%) Found / Calculated | H (%) Found / Calculated | (N (%)) Found / Calculated |
|---|---|---|---|---|
| 1' | C₁₃H₁₇ClN₂O₃ | 55.03 / 54.84 | 5.92 / 6.02 | 9.67 / 9.84 |
| 2' | C₁₄H₁₉ClN₂O₃ | 56.09 / 56.28 | 6.60 / 6.41 | 9.28 / 9.38 |
| 3' | C₁₅H₂₁ClN₂O₃ | 57.39 / 57.60 | 6.57 / 6.77 | 9.16 / 8.96 |
| 4' | C₁₅H₂₁ClN₂O₃ | 57.82 / 57.60 | 6.98 / 6.77 | 8.89 / 8.96 |
| 5' | C₁₅H₂₁ClN₂O₃ | 57.42 / 57.60 | 6.95 / 6.77 | 8.76 / 8.96 |
| 6' | C₁₆H₂₃ClN₂O₃ | 58.53 / 58.80 | 7.31 / 7.09 | 8.42 / 8.57 |
| 7' | C₁₆H₁₅ClN₂O₃ | 60.23 / 60.29 | 4.68 / 4.74 | 8.77 / 8.79 |
| 8' | C₁₆H₁₄Cl₂N₂O₃ | 54.30 / 54.41 | 4.15 / 4.00 | 7.79 / 7.93 |
| 9' | C₁₇H₁₇ClN₂O₃ | 61.19 / 61.36 | 5.34 / 5.15 | 8.54 / 8.42 |
| 10' | C₁₂H₁₂ClF₃N₂O₃ | 44.23 / 44.39 | 3.64 / 3.73 | 8.43 / 8.63 |
| 11' | C₁₃H₁₃ClF₄N₂O₃ | 43.98 / 43.77 | 3.81 / 3.67 | 7.85 / 7.85 |
| 12' | C₁₃H₁₂ClF₅N₂O₃ | 41.85 / 41.67 | 3.38 / 3.23 | 7.36 / 7.48 |
| 13' | C₁₄H₁₃ClF₆N₂O₃ | 41.16 / 41.35 | 3.37 / 3.22 | 6.84 / 6.89 |
| 14' | C₁₄H₁₂ClF₇N₂O₃ | 39.81 / 39.59 | 3.01 / 2.85 | 6.40 / 6.60 |
| 15' | C₁₅H₁₃ClF₈N₂O₃ | 39.25 / 39.45 | 2.79 / 2.87 | 5.93 / 6.13 |
| 16' | C₁₇H₁₃ClF₁₂N₂O₃ | 36.92 / 36.68 | 2.75 / 2.35 | 5.04 / 5.03 |

TABLE 5

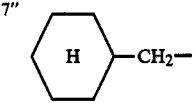
(III)

| No. | R | Yield of synthesis (%) | Melting point (°C.) | NMR Spectrum (CDCl$_3$, δ, ppm, 60MHz) |
|---|---|---|---|---|
| 1″ | CH$_3$(CH$_2$)$_2$— | 79.2 | Oil | 0.92(3H, t, 7Hz), 1.63(2H, 6-plet, 7Hz), 3.45(2H, t, 7Hz), 4.49(2H, s), 4.98(2H, bs), 5.80(1H, bs), 6.7~7.5(6H, m) |
| 2″ | CH$_3$(CH$_2$)$_3$— | 83.5 | Oil | 0.90(3H, t, 6Hz), 1.0~2.0(4H, m), 3.47(2H, t, 6Hz), 4.43(2H, s), 5.00(2H, bs), 5.93 (1H, bs), 6.6~7.7(6H, m) |
| 3″ | CH$_3$(CH$_2$)$_4$— | 84.0 | Oil | 0.88(3H, t, 6Hz), 1.0~1.8(6H, m), 3.48(2H, t, 6Hz), 4.48(2H, s), 4.87(2H, bs), 5.65 (1H, bs), 6.6~7.5(6H, m) |
| 4″ | (CH$_3$)$_2$CH(CH$_2$)$_2$— | 80.6 | Oil | 0.90(6H, d, 6Hz), 1.1~2.2(3H, m), 3.50(2H, t, 6Hz), 4.47(2H, s), 4.93(2H, bs), 5.77 (1H, bs), 6.5~7.6(6H, m) |
| 5″ | (CH$_3$)$_3$CCH$_2$— | 76.3 | 140~142 | 0.93(9H, s), 3.33(2H, s), 4.45(2H, s). 5.33(2H, bs), 6.16(1H, bs), 6.6~7.6(6H, m) |
| 6″ | CH$_3$(CH$_2$)$_5$— | 80.5 | 55~58 | 0.90(3H, t, 6Hz), 1.0~1.9(8H, m), 3.48(2H, t, 6Hz), 4.80(2H, bs), 5.50(1H, bs), 6.2~7.7(6H, m) |
| 7″ | 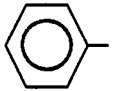 | 78.5 | 106~108 | 0.8~1.05(2H, m), 1.05~1.3(3H, m), 1.5~1.8(6H, m), 3.27(2H, d, 6.34Hz), 4.47(2H, s), 5.44(1H, bs), 6.50(1H, s), 6.86(1H, d, 7.8Hz), 6.96(1H, dd, 7.8, 1.9Hz), 7.06(1H, bs), 7.23(1H, t, 7.8Hz)** |
| 8″ | CH$_2$=CHCH$_2$— | 75.6 | 70~72 | 4.04(2H, dt, 5.4, 1.5Hz), 4.51(2H, s), 5.21(1H, dq, 10.3, 1.5Hz), 5.31(1H, dq, 17.1, 1.5Hz), 5.96(1H, ddt, 17.1, 10.3, 5.4Hz), 6.88(1H, d, 7.8Hz), 6.98(1H, dd, 7.8, 1.9Hz), 7.08(1H, bs), 7.24(1H, t, 7.8Hz), 4.71(2H, bs), 5.32(1H, bs)** |
| 9″ | CH$_3$(CH$_2$)$_3$O(CH$_2$)$_2$— | 78.0 | 133~134 | 0.85(3H, t, 7.3Hz), 1.30(2H, 6-plet, 7.3Hz), 1.52(2H, tt, 7.3, 6.8Hz), 3.01(5H, s), 3.41(2H, t, 6.8Hz), 3.56(4H, s), 4.48(2H, s), 6.74(1H, d, 7.8Hz), 6.94(1H, dd, 7.8, 1.5Hz), 7.01(1H, bs), 7.15(1H, t, 7.8Hz)** |
| 10″ | 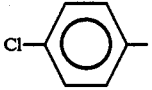 | 84.8 | 135~138 | 5.00(2H, s), 5.4(2H, bs), 6.2(1H, bs), 6.7~7.5(10H, m), 7.67(1H, bs)* |
| 11″ | 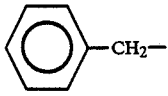 | 92.5 | 145~148 | 4.98(2H, s), 5.4(2H, bs), 6.3(1H, bs), 6.7~7.5(9H, m), 7.73(1H, bs) |
| 12″ |  | 73.5 | 63~65 | 4.59(4H, s), 4.80(2H, bs), 5.50(1H, bs), 6.6(2H, bs), 6.7~7.6(10H, m) |
| 13″ | CF$_3$CH$_2$— | 87.2 | 80~82 | 3.78(2H, q, 9Hz), 4.60(2H, s), 5.20(2H, bs), 5.93(1H, bs), 6.6~7.5(6H, m)* |
| 14″ | CHF$_2$CF$_2$CH$_2$— | 78.3 | 73~74 | 3.80(2H, tt, 13, 1.5Hz), 4.57(2H, s), 4.9(2H, bs), 5.8(1H, bs), 5.93(1H, tt, 53, 6.5Hz), 6.7~7.6(6H, m) |
| 15″ | CF$_3$CF$_2$CH$_2$— | 88.7 | 95~97 | 3.85(2H, tt, 13.2Hz), 4.60(2H, bs), 4.85 (2H, bs), 5.6(1H, bs), 6.6~7.4(6H, m) |
| 16″ | CF$_3$CHFCF$_2$CH$_2$— | 80.3 | Oil | 3.53~4.10(2H, m), 4.53(2H, s), 4.93(2H, bs), 5.6(1H, bs), 5.0(1H, d, 6-plet, 50, 6Hz), 6.7~7.6(6H, m) |
| 17″ | CF$_3$(CF$_2$)$_2$CH$_2$— | 87.5 | 85~87 | 3.90(2H, tt, 13.5, 2Hz), 4.62(2H, s), 4.9 (2H, bs), 5.7(1H, bs), 6.7~7.5(6H, m) |
| 18″ | CHF$_2$(CF$_2$)$_3$CH$_2$— | 73.2 | Oil | 3.90(2H, tt, 13, 2Hz), 4.63(2H, s), 4.9(2H, bs), 5.67(1H, bs), 6.03(1H, tt, 52, 6Hz), 6.6~7.5(6H, m) |

TABLE 5-continued

(III) structure: HNN=C(CONH₂)(NH₂) attached to phenyl ring with CH₂OR substituent

| No. | R | Yield of synthesis (%) | Melting point (°C.) | NMR Spectrum (CDCl₃, δ, ppm, 60MHz) |
|---|---|---|---|---|
| 19" | $CHF_2(CF_2)_5CH_2-$ | 79.6 | 94~96 | 3.92(2H, tt, 13, 2Hz), 4.62(2H, s), 5.2(2H, bs), 5.83(1H, bs), 6.15(1H, tt, 52, 5Hz), 6.6~7.5(6H, m)* |

Notes:
*determined in a mixed solvent of CDCl₃ and d₆-acetone
**determined by an apparatus of 250 MHz

TABLE 6

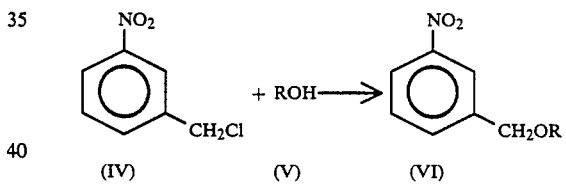

(III)

| No. | Molecular formula | C (%) Found / Calculated | H (%) Found / Calculated | N (%) Found / Calculated |
|---|---|---|---|---|
| 1" | $C_{12}H_{18}N_4O_2$ | 57.32 / 57.58 | 7.01 / 7.25 | 22.24 / 22.38 |
| 2" | $C_{13}H_{20}N_4O_2$ | 59.29 / 59.07 | 7.83 / 7.63 | 21.00 / 21.20 |
| 3" | $C_{14}H_{22}N_4O_2$ | 60.72 / 60.41 | 7.68 / 7.97 | 20.30 / 20.13 |
| 4" | $C_{14}H_{22}N_4O_2$ | 60.23 / 60.41 | 7.84 / 7.97 | 20.42 / 20.13 |
| 5" | $C_{14}H_{22}N_4O_2$ | 60.46 / 60.41 | 8.05 / 7.97 | 19.94 / 20.13 |
| 6" | $C_{15}H_{24}N_4O_2$ | 61.71 / 61.62 | 8.45 / 8.27 | 19.17 / 19.16 |
| 7" | $C_{16}H_{24}N_4O_2$ | 63.16 / 63.14 | 7.79 / 7.95 | 18.60 / 18.41 |
| 8" | $C_{12}H_{16}N_4O_2$ | 58.18 / 58.05 | 6.67 / 6.50 | 22.46 / 22.56 |
| 9" | $C_{15}H_{24}N_4O_3$ | 58.40 / 58.42 | 7.86 / 7.84 | 18.07 / 18.17 |
| 10" | $C_{15}H_{16}N_4O_2$ | 63.21 / 63.37 | 5.71 / 5.67 | 19.86 / 19.71 |
| 11" | $C_{15}H_{15}ClN_4O_2$ | 56.47 / 56.52 | 4.68 / 4.74 | 17.54 / 17.58 |
| 12" | $C_{16}H_{18}N_3O_2$ | 64.39 / 64.41 | 5.90 / 6.08 | 18.65 / 18.78 |
| 13" | $C_{11}H_{13}F_3N_4O_2$ | 45.58 / 45.52 | 4.70 / 4.51 | 19.11 / 19.30 |
| 14" | $C_{12}H_{14}F_4N_4O_2$ | 44.91 / 44.73 | 4.34 / 4.38 | 17.21 / 17.39 |
| 15" | $C_{12}H_{13}F_5N_4O_2$ | 42.46 / 42.36 | 4.00 / 3.85 | 16.66 / 16.47 |
| 16" | $C_{13}H_{14}F_6N_4O_2$ | 41.74 / 41.94 | 3.83 / 3.79 | 14.80 / 15.05 |
| 17" | $C_{13}H_{13}F_7N_4O_2$ | 39.83 / 40.01 | 3.52 / 3.36 | 14.19 / 14.36 |
| 18" | $C_{14}H_{14}F_8N_4O_2$ | 39.96 / 39.82 | 3.52 / 3.34 | 13.40 / 13.27 |
| 19" | $C_{16}H_{14}F_{12}N_4O_2$ | 36.72 / 36.80 | 2.89 / 2.70 | 10.81 / 10.73 |

The derivative of 4,5-1H-1,2,4-triazole-3-carboxamide according to the present invention can be produced via the compound represented by the formula (II) and the compound represented by the formula (III); while using 3-nitrobenzylchloride(IV) as a starting material.

Namely, 3-nitrobenzyl chloride(IV) is reacted with a compound represented by the formula (V):

$$ROH \qquad (V)$$

wherein R has the same meaning as above, in a solvent such as dimethylformamide, hexamethylphosphoramide, etc. for from 0.1 to 20 hours, preferably from 0.5 to 10 hours at a temperature of from −10° to 150° C., preferably from 0° to 80° C. in the presence of an acceptor for hydrogen chloride formed such as KOH, NaH, etc. to obtain a nitrobenzyl ether represented by the formula (VI):

(IV) + ROH ⟶ (VI) [3-nitrobenzyl chloride reacting with ROH to form 3-nitrobenzyl ether]

(IV)  (V)  (VI)

The thus obtained of nitrobenzyl ether (VI) is reduced by various well known methods. For instance, a method of heating the compound under reflux after adding hydrazine hydrate in alcohol for from 1 to 10 hours in the presence of palladium-charcoal into a derivative of aniline (VII).

Then, the thus obtained derivative of aniline (VII) is diazotized by an ordinary methiod, for example, by sodium nitrite in hydrochloric acid at a temperature of from −10° to 15° C. to obtain a diazonium salt (VIII):

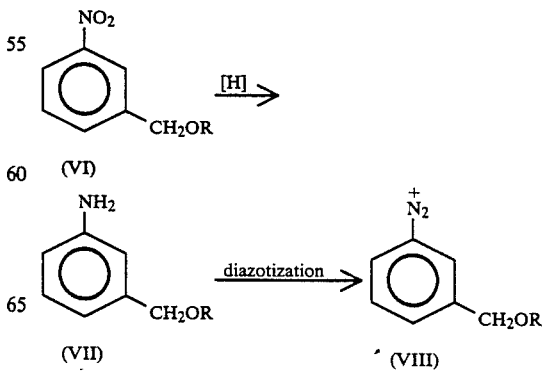

(VI) → (VII) → (VIII) via [H] and diazotization

The thus obtained diazonium salt (VIII) is reacted with methyl 2-chloroacetoacetate represented by the formula (IX):

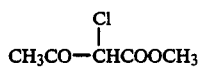

at a temperature of −10° to 50° C., preferably 0° to 30° C. in a solvent, for instance, aqueous methanol, etc. in the presence of base such as sodium acetate, sodium bicarbonate, etc. to obtain a derivative of methyl chlorophenylhydrazonoacetate (II):

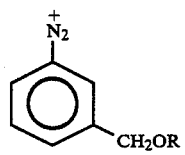 + CH₃CO—CHClCOOCH₃ ⟶

(VIII)                     (IX)

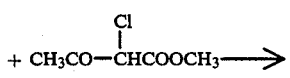

(II)

The derivative of methyl chlorophenylhydrazonoacetate (II) is reacted with ammonia in an alcohol such as methanol, ethanol, etc. for 1 to 50 hours at a temperature of −10° to 50° C., preferably 0° to 30° C. to obtain a phenylhydrazone derivative of oxamide (III):

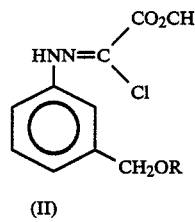

(II)                            (III)

Finally, the phenylhydrazone derivative of oxamide (III) and a non-substituted- or substituted benzaldehyde represented by the formula (X):

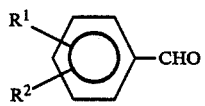

wherein R¹ and R² respectively have the same meaning as above, are subjected to dehydration reaction for 0.1 to 40 hours, preferably 1 to 20 hours, at a temperature of −10° to 150° C., preferably 10° to 100° C. in the presence of an acid catalyst, for instance, acetic acid, p-toluenesulfonic acid, etc., to obtain the derivative of 4,5-dihydro-1H-1,2,4-triazole-3-carboxamide according to the present invention.

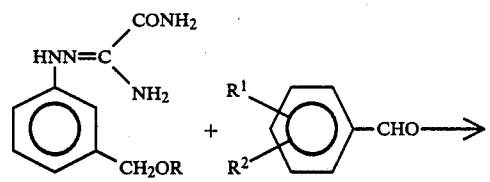

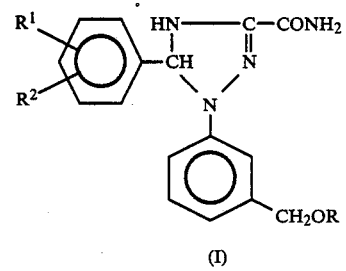

(I)

At the time of the above reaction, the derivative of 4,5-dihydro-1H-1,2,4-triazole-3-carboxamide is obtained in a higher yield when the reaction is carried out in an inert atmosphere.

The derivative of 4,5-dihydro-1H-1,2,4-triazole-3-carboxamide according to the present invention may be used singly or used as herbicidal composition such as wettable powder, emulsions, granules, powders, etc., while using a carrier (diluent) and/or adjuvant which have(has) been hitherto used for preparing agricultural chemical composition.

The content of the derivative of 4,5-dihydro-1H-1,2,4-triazole-3-carboxamide according to the present invention in a herbicidal composition is preferably 0.1 to 50% by weight.

The derivative of 4,5-dihydro-1H-1,2,4-triazole-3-carboxamide according to the present invention and a herbicidal composition containing the derivative as an active ingredient are applied onto the soil of a paddy field and a crop field and or weeds so that 0.1 to 500 g of the derivative is applied per 10 are of the surface area of the field.

The derivative of 4,5-dihydro-1H-1,2,4-triazole-3-carboxamide represented by the formula (I) according to the present invention, preferably the compounds Nos. 4, 5, 7, 13~19, 22, 25~27, 31~33, 36, 37, 40, 50 and 53, shows an excellent herbicidal activity without damaging the crop plants such as rice plant, wheat, corn, etc., and the derivative of methyl chlorophenylhydrazonoacetate represented by the formula (II) and the phenylhydrazone derivative of oxamide represented by the formula (III) are the useful intermediates for producing the derivative of 4,5-dihydro-B 1H-1,2,4-triazole-3-carboxamide.

The present invention will be explained more precisely while referring to the following non-limitative Examples.

SYNTHETIC EXAMPLE 1

Synthesis of 1-(3-methylbutoxy)methyl-3-nitrobenzene (the compound represented by the formula(VI) wherein R represents 3-methylbutyl group)

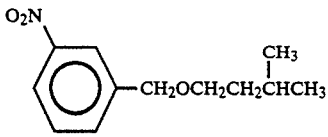

Into a mixture of 500 ml (4.59 mol) of 3-methyl-1-butanol and 140 ml of dimethylformamide, 158.1 g (0.92 mol) of 3-nitrobenzyl chloride was dissolved. While vigorously stirring the thus formed solution under cooling in a water bath, 78 g (1.39 mol) of pellets of potassium hydroxide were added to the solution. The temperature of the solution rised to 43° C. and then dropped slowly to room temperature. The reaction mixture was stirred for further 7 hours at room temperature to complete the reaction. After removing the solid matters in the reaction mixture by filtration and adjusting the filtrate to pH 2 with hydrochloric acid, the excess of alcohol and dimethylformamide were distilled off from the filtrate. The residue was dissolved into a mixed solvent of 450 ml of n-hexane and 50 ml of ethyl acetate, and the thus formed solution was washed with 1N hydrochloric acid and then with an aqueous saturated solution of sodium chloride and dried over anhydrous magnesium sulfate. After distilling the solvent off from the thus dried solution, the residue was subjected to fractional distillation to obtain 185.2 g of a fraction at 116°~117° C. (0.08 mmHg) in a yield of 90.1%.

SYNTHETIC EXAMPLE 2

Synthesis of 3-[(3-methylbutoxy)methyl]aniline (the compound represented by the formula (VII) wherein R represents a 3-methylbutyl group

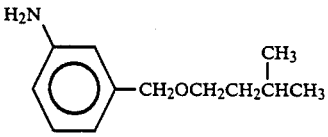

Into 150 ml of ethanol, 130 g (0.58 mol) of the derivative of nitrobenzyl ether obtained in Synthetic Example 1 was dissolved and 0.6 g of 10% palladium-charcoal was added to the thus formed solution. While stirring the thus formed mixture, 89 ml (1.84 mol) of hydrazine hydrate was dropped into the mixture at a speed of not causing the vigorous forming. After ending the dropping, the reaction mixture was heated for 3 hours under reflux to complete the reaction. After cooling the reaction mixture by allowing to stand, the catalyst was removed from the reaction mixture by filtration and the catalyst was washed with ethanol. The filtrate was condensed together with the washings and dissolved in 300 ml of dichloromethane. After washing the solution with an aqueous 10% solution of sodium carbonate and then with an aqueous saturated solution of sodium chloride, the thus washed solution was dried over anhydrous potassium carbonate. After distilling the solvent off from the dried solution, the residue was subjected to fractional distillation to obtain 109.2 g of a fraction at 105°~106° C. (0.19 mmHg) in a yield of 97.1%.

SYNTHETIC EXAMPLE 3

Synthesis of methyl chloro[3-[(3-methylbutoxy)methyl]phenylhydrazono]acetate (Compound No. 4')

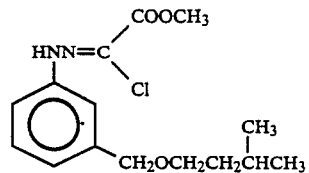

Into 30 ml of acetic acid, 19.3 g (0.1 ml) of 3-[(3-methylbutoxy)methyl]aniline obtained in Synthetic Example 2 was dissolved, and after adding 26 ml of concentrated hydrochloric acid to the thus formed solution, the mixture was cooled to 0° C. By dropping a solution prepared by dissolving 6.9 g (0.1 mol) of sodium nitrite to 12 ml of water to the thus cooled mixture so as to maintain the temperature of the mixture not higher than 5° C., an aqueous solution of a diazonium salt was prepared.

Separately, 15.1 g (0.1 mol) of methyl 2-chloroacetoacetate was added to a mixture of 70 ml of methanol, 50 ml of water and 40.8 g (0.3 mol) of sodium acetate trihydrate, and the thus formed mixture was cooled to 0° C. Into the thus cooled mixture, the aqueous solution of the diazonium salt prepared above was added within 15 min and the mixture was stirred for one hour at 0° C. and for 3 hours at room temperature. Then, 100 ml of water was added to the miture, and it was extracted two times with each 150 ml of benzene. After washing the organic layer with water, an aqueous saturated solution of sodium hydrogen carbonate and an aqueous saturated solution of sodium chloride, the thus washed layer was dried over anhydrous sodium sulfate.

The oily substance obtained by distilling the solvent off from the thus dried layer was purified by silica-gel chromatography while using dichloromethane as an eluent to obtain 29.3 g of a pale yellow oily substance in a yield of 92.8%.

SYNTHETIC EXAMPLE 4

Synthesis of methyl chloro[3-(phenoxymethyl)phenylhydrazono]acetate (compound No. 7')

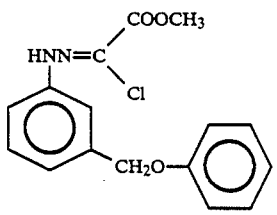

Into 15 ml of acetic acid, 10.0 g (0.05 mol) of 3-(phenoxymethyl)aniline obtained in the same manner as in Synthetic Examples 1 and 2 was dissolved and after adding 13 ml of concentrated hydrochloric acid to the thus formed solution, the mixture was cooled to 0° C. Into the thus cooled mixture, a solution prepared by dissolving 3.5 g (0.05 mol) of sodium nitrite into 6 ml of water was dropped while maintaining the mixture at a temperature of not higher than 5° C. to prepare an aqueous solution of a diazonium salt.

Separately, 7.5 g (0.05 mol) of methyl 2-chloroacetoacetate were added to a mixture of 35 ml of methanol, 25 ml of water and 20.4 g (0.15 mol) of sodium acetate trihydrate and the mixture was cooled to 0° C.

Into the thus formed mixture, the aqueous solution of a diazonium solution previously prepared was dropped and the mixture was stirred for one hour at 0° C. and then for 3 hours at room temperature. The thus precipitated crystals were collected by filtration, washed with water and dried. By recrystallizing the thus collected crystals from a mixed solvent of dichloromethane and carbon tetrachloride, 14.6 g of crystals melting at 115°~117° C. were obtained in a yield of 91.2%.

SYNTHETIC EXAMPLE 5

Synthesis of oxamide 3-[(3-methylbutoxy)methyl]phenylhydrazone (Compound No. 4″)

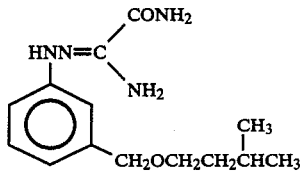

A soultion of 15.9 g (0.05 mol) of the derivative of methyl chlorophenylhydrazonoacetate obtained in Synthetic Example 3 in 20 ml of dichloromethane was carefully added to 100 ml of an ice-cooled 20% solution of ammonia in methanol, and after stirring the mixture for 30 min, the thus formed mixture was allowed to stand overnight with a close stopper. The residue obtained by distilling the solvent off from the mixture was extracted with a mixture of ethyl acetate and water and the organic layer was separated. After washing the organic layer with water and then with an aqueous saturated solution of sodium chloride, and drying the thus washed layer over anhydrous sodium sulfate, the solent was distilled off. The thus obtained brown oily substance was purified by silica-gel chromatography while using a 4:1 (by volume) mixed solvent of dichloromethane and ethyl acetate as an eluent to obtain 11.4 g of a pale yellow oily substance in a yield of 80.6%.

SYNTHETIC EXAMPLE 6

Synthesis of oxamide 3-(phenoxymethyl)phenylhydrazone (Compound No. 10″)

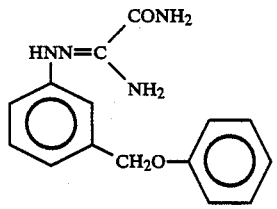

A solution of 12.7 g (0.04 mol) of the derivative of methyl chlorophenylhydrazonoacetate obtained in Synthetic Example 4 in 30 ml of dichloromethane was carefully added into 100 ml of a 20% solution of ammonia in methanol and after stirring the thus formed mixture for 30 min, the mixture was allowed to stand overnight with a close stopper. The residue obtained by distilling the solvent off from the mixture was dispersed into ethyl acetate and water and the organic layer was collected. After washing the organic layer with water and then with an aqueous saturated solution of sodium chloride, and drying the thus washed layer over anhydrous sodium sulfate, the solvent was distilled off from the thus dried organic layer.

The thus obtained crude product was recrystallized from ethyl acetate to obtain 9.6 g of pale yellow crystals in a yield of 84.8%.

EXAMPLE 1

Synthesis of 4,5-dihydro-1-[3[(3-methylbutoxy)methyl]phenyl]-5-phenyl-1H-1,2,4-triazole-3-carboxamide Compound No. 4)

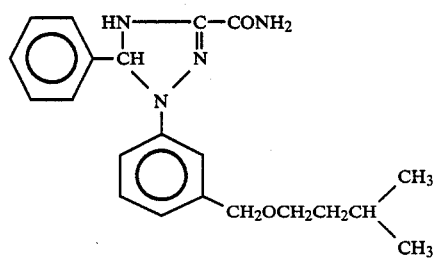

Into 12 ml of acetic acid saturated with nitrogen, 2.78 g (0.01 mol) of the derivative of oxamide obtained in Synthetic Example 5 was dissolved, and 1.17 g (0.01 mol) of benzaldehyde was added to the solution under nitrogen atmosphere, and the mixture was stirred for 16 hours at room temperature. Then, water saturated with nitrogen was added to the mixture and the precipitated crystals were collected by filtration and dried under vacuum.

By recrystallizing the thus collected crystals from a mixed solvent, saturated with nitrogen, of ethyl acetate and n-hexane, 3.11 g of 4,5-dihydro-1-[3-[(3-methylbutoxy)methyl]phenyl]-5-phenyl-1H-1,2,4-triazole-3-carboxamide was obtained as yellow acicular crystals melting at 144°~146° C. in a yeild of 84.4%.

EXAMPLE 2

Synthesis of 4,5-dihydro-1-[3-(phenoxymethyl)phenyl]-5-phenyl-1H-1,2,4-triazole-3-carboxamide (Compound No. 10)

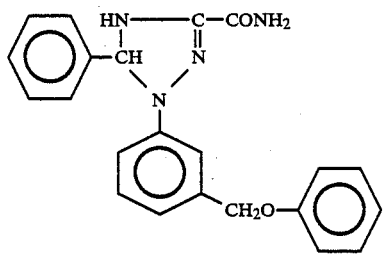

Into 15 ml of acetic acid saturated with nitrogen, 2.84 g (0.01 mol) of oxamide 3-(phenoxymethyl)phenylhydrazone obtained in Synthetic Example 6 was dissolved, and 1.17 g (0.011 mol) of benzaldehyde was added to the thus prepared solution under nitrogen atmosphere, and the mixture was stirred for 16 hours at room temperature. Into the mixture, water saturated with nitrogen was added, and the prrecipitated crystals were collected by filtration and dried under vacuum.

The thus collected crystals were recrystallized from a mixture, saturated with nitrogen, of ethyl acette and n-hexane to obtain 3.18 g of 4,5-dihydro-1-[3-(phenoxymethyl)phenyl]-5-phenyl-1H-1,2,4-triazole-3-carboxamide melting at 177°~178° C. in a yield of 85.5%.

EXAMPLE 3

Synthesis of
1-[3-[(2,2,3,3,3-pentafluoropropoxy)methyl]phenyl]-4,5-dihydro-5-phenyl-1H-1,2,4-triazole-3-carboxamide
(Compound No. 15)

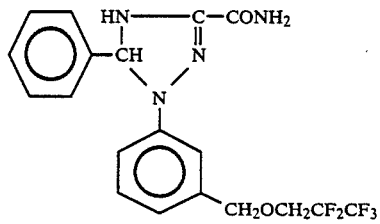

Into 6 ml of acetic acid saturated with nitrogen, 1.02 g (3.0 mmol) of oxamide 3-[(2,2,3,3,3-pentafluoropropoxyl)methyl]phenylhydrazone obtained in the same manner as in Synthetic Examples 1 to 6 was dissolved, and 0.35 g (3.3 mmol) of benzaldehyde was added to the thus formed solution under nitrogen atmosphere, and the mixture was stirred for 16 hours at room temperature. Then, water saturated with nitrogen was added to the mixture, and the precipitated crystals were collected by filtration and dried under vacuum. The thus dried crystals were recrystallized from a mixture, saturated with nitrogen, of ethyl acetate and n-hexane to obtain 1.19 g of 1-[3-[(2,2,3,3,3-pentafluoropropoxy)methyl]phenyl]-4,5-dihydro-5-phenyl-1H-1,2,4-triazole-3-carboxamide melting at 146°-148° C. in a yield of 92.7%.

EXAMPLE 4

Synthesis of
1-[3-(cyclohexylmethoxy)methyl]phenyl-4,5-dihydro-5-phenyl-1H-1,2,4-triazole-3-carboxamide (Compound No. 7)

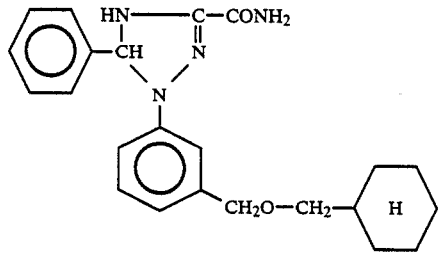

Into 3.3 ml of acetic acid saturated with nitrogen, 502 mg (1.65 mmol) of oxamide [3-(cyclohexylmethoxy)methyl]phenylhydrazone was dissolved, and 193 mg (1.81 mmol) of benzaldehyde was added to the solution, and the mixture was stirred for 20 hours at room temperature.

After adding water saturated with nitrogen to the mixture, the precipitated crystals were collected by filtration and dried under vacuum. The thus dried crystals were dissolved in 40 to 50 ml of dichloromethane saturated with nitrogen, and about 40 ml of n-hexane were added to the solution little by little to precipitate 616.3 mg of the crystals of 1-[3-(cyclohexylmethoxymethyl)phenyl]-4,5-dihydro-5-phenyl-1H-1,2,4-triazole-3-carboxamide melting at 165°-167° C. in a yield of 95.2%.

EXAMPLE 5

Synthesis of
5-(2-fluorophenyl)-4,5-dihydro-1-[3-[(3-methylbutoxyl)methyl]phenyl]-1H-1,2,4-triazole-3-carboxamide
(Compound No. 22)

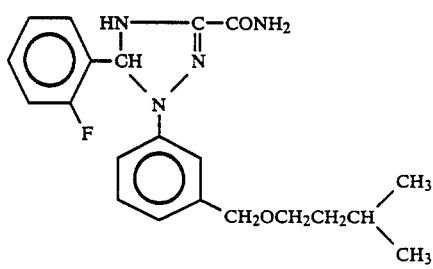

Into 12 ml of acetic acid saturated with nitrogen 2.78 g (0.01 mol) of the derivative of oxamide obtained in Synthetic Example 5 was dissolved, and 1.36 g (0.011 mol) of 2-fluorobenzaldehyde was added to the thus formed solution under nitrogen atmosphere, and the mixture was stirred for 16 hours at room temperature. After adding water saturated with nitrogen to the mixture, the precipitated crystals were collected by filtration and dried under vacuum. The thus dried crystals were recrystallized from a mixed solvent, saturated with nitrogen, of ethyl acetate and n-hexane to obtain 3.03 g of 5-(2-fluorophenyl)-4,5-dihydro-1-[3-[(3-methylbutoxy)methyl]phenyl]-1H-1,2,4-triazole-3-carboxamide melting at 120°-122° C. in a yield of 78.9%.

EXAMPLE 6

Synthesis of
5-(2-fluorophenyl)-4,5-dihydro-1-[3-(phenoxymethyl)-phenyl]-1H-1,2,4-triazole-3-carboxamide (Compound No. 28)

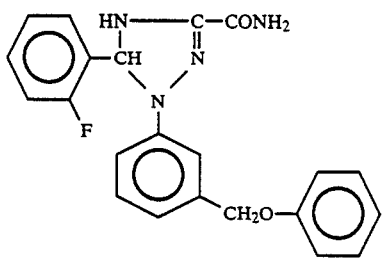

Into 15 ml of acetic acid saturated with nitrogen, 2.84 g (0.01 mol) of oxamide 3-(phenoxymethyl)phenylhydrazone was dissolved, and 1.36 g (0.011 mol) of 2-fluorobenzaldehyde was added to the thus formed solution under nitrogen atmosphere and the mixture was stirred for 16 hours at room temperature. After adding water saturated with nitrogen to the mixture, the precipitated crystals were collected by filtration and dried under vacuum. The thus dried crystals were recrystallized from a mixed solvent, saturated with nitrogen, of ethyl acetate and n-hexane to obtain 3.38 g of 5-(2-fluorophenyl)-4,5-dihydro-1-[3-(phenoxymethyl)-phenyl]-1H-1,2,4-triazole-3-carboxamide melting at 176°–178° C. in a yield of 86.7%.

EXAMPLE 7

Synthesis of 5-(2-fluorophenyl)-1-[3-[(2,2,3,3,3-pentafluoropropoxy)methyl]phenyl]-4,5-dihydro-1H-1,2,4-triazole-3-carboxamide (Compound No. 33)

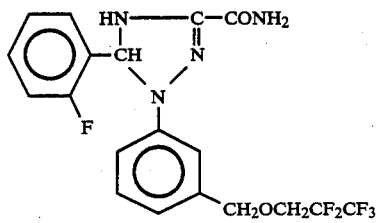

Into 6 ml of acetic acid saturated with nitrogen, 1.02 g (3.0 mmol) of oxamide 3-[(2,2,3,3,3-pentafluoropropoxy)methyl]phenylhydrazone obtained in the same manner as in Synthetic Examples 1 to 6 was dissolved, and after adding 0.41 g (3.3 mmol) of 2-fluorobenzaldehyde to the thus formed solution under nitrogen atmosphere, the mixture was stirred for 16 hours at room temperature.

To the mixture, water saturated with nitrogen was added, and the precipitated crystals were collected by filtration and dried under vacuum. The thus dried crystals were recrystallized from a mixed solvent, saturated with nitrogen, of ethyl acetate and n-hexane to obtain 1.08 g of 5-(2-fluorophenyl)-1-[3-[(2,2,3,3,3-pentafluoropropoxy)methyl]phenyl]-4,5-dihydro-1H-1,2,4-triazole-3-carboxamide melting at 151°–153° C. in a yield of 80.7%.

EXAMPLE 8

Synthesis of 1-[3-[(cyclohexylmethoxy)methyl]phenyl]-5-(2-fluorophenyl)-4,5-dihydro-1H-1,2,4-triazole-3-carboxamide (Compound No. 27)

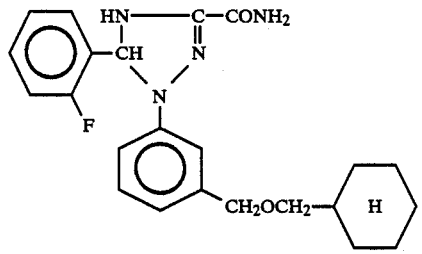

Into 3.3 ml of acetic acid saturated with nitrogen, 508 mg (1.67 mmol) of oxamide 3-[(cyclohexylmethoxy)methyl]phenylhydrazone was dissolved and after adding 228 mg (1.84 mmol) of 2-fluorobenzaldehyde to the solution, the mixture was stirred for 20 hours at room temperature.

To the mixture, water saturated with nitrogen was added, and the precipitated crystals were collected by filtration and dried under vacuum. The thus dried crystals were dissolved in 40 ml of dichloromethane saturated with nitrogen and 40 ml of n-hexane were added little by little to the solution to obtain 656 mg of the crystlas of 1-[3-[(cyclohexylmethoxy)methyl]phenyl]-5-(2-fluorophenyl)-4,5-dihydro-1H-1,2,4-triazole-3-carboxamide melting at 148°–149° C. in a yield of 95.8%.

EXAMPLE 9

Preparation Of A Herbicidal Composition Of Wettable Powder 50 parts by weight of Compound No. 4 of Table 1,
5 parts by weight of a salt of ligninsulfonic acid,
3 parts by weight of a salt of alkylsulfonic acid and
42 parts by weight of diatomaceous earth.

A mixture of the above substances were pulverized to obtain a herbicidal composition of a wettable powder form.

The thus obtained herbicidal composition is applied after diluting with water.

EXAMPLE 10

Preparations Of A Herbicidal Composition Of Emulsion 25 parts by weight of Compound No. 4 of Table 1,
65 parts by weight of xylene and
10 parts by weight of polyoxyethylene alkyl allyl ether.

The above substances were uniformly blended to obtain a herbicidal composition of emulsion form.

The thus prepared herbicidal composition is applied after diluting with water.

EXAMPLE 11

Preparation Of A Herbicidal Composition Of Granule 8 parts by weight of Compound No. 17 of Table 1,
40 parts by weight of bentonite,
45 parts by weight of clay and
7 parts by weight of a salt of ligninsulfonic acid.

The above substances were uniformly blended and after adding water to the thus formed blend, the mixture was kneaded and extruded into granules while using an extruding pelletizer.

The thus extruded granules were dried to be the herbicidal composition of granule form.

By using each of the other derivatives of 4,5-dihydro-1H-1,2,4-triazole-3-carboxamide shown in Table 1, the herbicidal compositions of wettable powder form, emulsion form and granule form were respectively prepared in the same manner as in Example 9 to 11.

EXAMPLE 12

Herbicidal Effect On Weeds In The Crop Field (Pre-emergence Treatment)

In a planter of the dimensions of 650×210×220 mm, soil was filled in a state of a crop field, and after sowing a predetermined amount of the seeds of *Amaranthus retroflexus, Bidens pilosa* var. *pilosa, Brassica arvensis, Stellaria media, Solanum nigrum, Abutilon theophrasti, Echinochloa Crus-galli* var. *frumentacea, Digitaria sanguinalis,* wheat and corn on the thus filled soil and covering the thus sown seeds with the soil, a dilution (prepared by diluting a wettable powder prepared in the same manner as in Example 9 to a predetermined concentration with water) was uniformly applied onto the soil of the planter in an amount corresponding to 200 g of the active ingredient of the wettable powder per 10 are of the surface of the soil in the planter, and thereafter, the thus treated planter was kept in a glass house at ordinary temperature to observe the growth state of the thus sown seeds.

On the 21st day of the treatment, the herbicidal effect of the wettable powder to each of the weeds and the phytotoxicity of the wettable powder to each of the crop plants were observed, and after evaluating the herbicidal effect and the phytotoxicity according to the following ratings, the results shown in Table 7 was obtained.

Ratings for evaluation:

(1) Herbicidal effect:
0 ... no herbicidal effect
1 ... not more than 30% of herbicidal effect
2 ... from 31 to 50% of herbicidal effect
3 ... from 51 to 70% of herbicidal effect
4 ... from 71 to 90% of herbicidal effect
5 ... from 91 to 100% of herbicidal effect.

(2) Phytotoxicity:
− ... no damage, ± ... slight damage,
+ ... moderate damage, ++ ... strong damage and
+++ ... extensive damage.

EXAMPLE 13

Herbicidal Effect on Weeds in the Crop Field
(Post-Emergence Treatment)

In the same manner as in Example 12, the seeds of the same plants as in Example 12 were sown on the soil in a planter, and at the time when each of the plants grew to the one to two lead-stage, a dilution prepared in the same way as in Example 12 from a wettable powder prepared in the same way as in Example 9 was uniformly applied on the plants and the surface of the soil in planter in the same amount as in Example 12. The thus treated planter was kept in a glass house. On the 21st day of the treatment, the herbicidal activity and the phytotoxicity were observed and evaluated according to the same ratings as in Example 12.

The results are shown in Table 8.

EXAMPLE 14

Herbicidal Effect on Weeds in the Paddy Field

After introducing water into a Wagner pot filled with a soil of the ordinary paddy field, thereby covering the soil in the pot with water, the seeds of *Echinochloa Crus-galli* var. *hispidula*, *Scirpus juncoides* subsp. *Hotarui*, *Alisma canalicalatum*, *Monochoria vaginalis* and *Cyperus difformis* were sown on the soil and the tubers of *Sagittaria pygmaea* and *Cyperus serotinus* were planted in the soil. After further transplanting two seedlings of rice plant (variety Sasanishiki) at the two-leaf stage to the pot, the pot was kept in a glass house for 3 days, and then a dilution prepared by diluting an emulsion prepared in the same manner as in Example 10 to a predetermined concentration was uniformly sprinkle onto the surface of water in the pot in the same amount as in Example 12 (200 g of the active ingredient per 10 ares). On the 21st day of the treatment, the herbicidal effect on the weeds and the phytotoxicity to the rice plant were observed and evaluated according to the same ratings as in Example 12. The results are shown in Table 9.

TABLE 7

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1 | 5 | 5 | 5 | 5 | 5 | 5 | 5 | 5 | − | − |
| 2 | 5 | 5 | 5 | 5 | 5 | 5 | 5 | 5 | − | ± |
| 3 | 5 | 5 | 5 | 5 | 5 | 5 | 5 | 5 | − | − |
| 4 | 5 | 5 | 5 | 5 | 5 | 5 | 5 | 5 | − | ± |
| 5 | 5 | 5 | 5 | 5 | 5 | 5 | 4 | 5 | − | − |
| 6 | 5 | 5 | 5 | 5 | 5 | 5 | 4 | 5 | − | − |
| 7 | 5 | 5 | 5 | 5 | 5 | 5 | 5 | 5 | − | − |
| 8 | 5 | 5 | 5 | 5 | 5 | 5 | 5 | 5 | − | − |
| 9 | 5 | 5 | 5 | 5 | 5 | 5 | 5 | 5 | − | − |
| 10 | 5 | 5 | 5 | 5 | 5 | 5 | 5 | 5 | − | − |
| 11 | 5 | 5 | 5 | 5 | 5 | 5 | 4 | 5 | − | − |
| 12 | 5 | 5 | 5 | 5 | 5 | 5 | 5 | 5 | − | − |
| 13 | 5 | 5 | 5 | 5 | 5 | 5 | 5 | 5 | − | ± |
| 14 | 5 | 5 | 5 | 5 | 5 | 5 | 5 | 5 | − | ± |
| 15 | 5 | 5 | 5 | 5 | 5 | 5 | 5 | 5 | − | ± |
| 16 | 5 | 5 | 5 | 5 | 5 | 5 | 5 | 5 | − | ± |
| 17 | 5 | 5 | 5 | 5 | 5 | 5 | 5 | 5 | ± | + |
| 18 | 5 | 5 | 5 | 5 | 5 | 5 | 5 | 5 | ± | ± |
| 19 | 5 | 5 | 5 | 5 | 5 | 5 | 5 | 5 | − | ± |
| 20 | 5 | 5 | 5 | 5 | 5 | 5 | 5 | 5 | − | ± |
| 21 | 5 | 5 | 5 | 5 | 5 | 5 | 5 | 5 | − | ± |
| 22 | 5 | 5 | 5 | 5 | 5 | 5 | 5 | 5 | − | ± |
| 23 | 4 | 5 | 5 | 5 | 5 | 5 | 5 | 5 | − | − |
| 24 | 5 | 5 | 5 | 5 | 5 | 5 | 5 | 5 | − | − |
| 25 | 5 | 5 | 5 | 5 | 5 | 5 | 5 | 5 | − | ± |
| 26 | 5 | 5 | 5 | 5 | 5 | 5 | 5 | 5 | − | ± |
| 27 | 5 | 5 | 5 | 5 | 5 | 5 | 5 | 5 | − | − |
| 28 | 5 | 5 | 5 | 5 | 5 | 5 | 4 | 5 | − | − |
| 29 | 5 | 5 | 5 | 5 | 5 | 5 | 4 | 5 | − | − |
| 30 | 5 | 5 | 5 | 5 | 5 | 5 | 5 | 5 | − | − |
| 31 | 5 | 5 | 5 | 5 | 5 | 5 | 5 | 5 | − | ± |
| 32 | 5 | 5 | 5 | 5 | 5 | 5 | 5 | 5 | − | ± |
| 33 | 5 | 5 | 5 | 5 | 5 | 5 | 5 | 5 | ± | + |
| 34 | 5 | 5 | 5 | 5 | 5 | 5 | 5 | 5 | ± | ± |
| 35 | 5 | 5 | 5 | 5 | 5 | 5 | 5 | 5 | ± | ± |
| 36 | 5 | 5 | 5 | 5 | 5 | 5 | 5 | 5 | ± | ± |
| 37 | 5 | 5 | 5 | 5 | 5 | 5 | 5 | 5 | − | ± |
| 38 | 5 | 5 | 5 | 5 | 5 | 5 | 5 | 5 | ± | ± |

TABLE 7-continued

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 39 | 5 | 5 | 5 | 5 | 5 | 5 | 5 | 5 | − | ± |
| 40 | 5 | 5 | 5 | 5 | 5 | 5 | 5 | 5 | ± | + |
| 41 | 5 | 5 | 5 | 5 | 4 | 5 | 4 | 5 | − | − |
| 42 | 4 | 5 | 5 | 5 | 5 | 5 | 5 | 5 | − | + |
| 43 | 5 | 5 | 5 | 5 | 4 | 5 | 4 | 5 | − | − |
| 44 | 5 | 5 | 5 | 5 | 5 | 5 | 5 | 5 | − | ± |
| 45 | 5 | 5 | 5 | 5 | 5 | 5 | 4 | 5 | − | − |
| 46 | 3 | 5 | 5 | 5 | 2 | 2 | 2 | 3 | − | − |
| 47 | 5 | 5 | 5 | 5 | 3 | 4 | 4 | 4 | − | − |
| 48 | 5 | 5 | 5 | 5 | 5 | 5 | 5 | 5 | − | ± |
| 49 | 5 | 5 | 5 | 5 | 5 | 5 | 5 | 5 | − | ± |
| 50 | 5 | 5 | 5 | 5 | 5 | 5 | 5 | 5 | − | + |
| 51 | 5 | 5 | 5 | 5 | 5 | 5 | 5 | 5 | − | ± |
| 52 | 5 | 5 | 5 | 5 | 5 | 5 | 4 | 5 | ± | + |
| 53 | 5 | 5 | 5 | 5 | 5 | 5 | 5 | 5 | + | + |

TABLE 8

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1 | 5 | 5 | 5 | 5 | 5 | 5 | 2 | 2 | − | − |
| 2 | 5 | 5 | 5 | 5 | 5 | 5 | 2 | 2 | ± | ± |
| 3 | 5 | 5 | 5 | 5 | 5 | 5 | 3 | 4 | − | − |
| 4 | 5 | 5 | 5 | 5 | 5 | 5 | 4 | 4 | ± | + |
| 5 | 5 | 5 | 5 | 5 | 5 | 5 | 3 | 3 | − | − |
| 6 | 5 | 5 | 5 | 5 | 5 | 5 | 3 | 3 | ± | ± |
| 7 | 5 | 5 | 5 | 5 | 5 | 5 | 2 | 2 | − | − |
| 8 | 5 | 5 | 5 | 5 | 5 | 4 | 2 | 2 | − | − |
| 9 | 5 | 5 | 5 | 5 | 5 | 5 | 2 | 3 | − | − |
| 10 | 5 | 5 | 5 | 5 | 5 | 5 | 2 | 2 | − | − |
| 11 | 5 | 5 | 5 | 5 | 5 | 5 | 2 | 3 | − | − |
| 12 | 5 | 5 | 5 | 5 | 5 | 5 | 2 | 2 | − | − |
| 13 | 5 | 5 | 5 | 5 | 5 | 5 | 2 | 2 | − | − |
| 14 | 5 | 5 | 5 | 5 | 5 | 5 | 2 | 2 | − | − |
| 15 | 5 | 5 | 5 | 5 | 5 | 5 | 5 | 5 | ± | + |
| 16 | 5 | 5 | 5 | 5 | 5 | 5 | 3 | 3 | ± | + |
| 17 | 5 | 5 | 5 | 5 | 5 | 5 | 5 | 5 | + | + |
| 18 | 5 | 5 | 5 | 5 | 5 | 5 | 3 | 4 | + | + |
| 19 | 5 | 5 | 5 | 5 | 5 | 5 | 4 | 4 | ± | + |
| 20 | 5 | 5 | 5 | 5 | 5 | 5 | 3 | 3 | − | ± |
| 21 | 5 | 5 | 5 | 5 | 5 | 5 | 2 | 3 | − | ± |
| 22 | 5 | 5 | 5 | 5 | 5 | 5 | 2 | 2 | − | ± |
| 23 | 5 | 5 | 5 | 5 | 5 | 5 | 3 | 4 | − | − |
| 24 | 5 | 5 | 5 | 5 | 5 | 5 | 2 | 3 | − | − |
| 25 | 3 | 5 | 5 | 5 | 5 | 5 | 2 | 2 | − | ± |
| 26 | 5 | 5 | 5 | 5 | 5 | 5 | 4 | 3 | − | ± |
| 27 | 5 | 5 | 5 | 5 | 5 | 5 | 2 | 3 | − | − |
| 28 | 5 | 5 | 5 | 5 | 5 | 5 | 3 | 3 | − | − |
| 29 | 5 | 5 | 5 | 5 | 5 | 5 | 3 | 4 | − | − |
| 30 | 5 | 5 | 5 | 5 | 3 | 4 | 3 | 3 | − | − |
| 31 | 5 | 5 | 5 | 5 | 5 | 5 | 3 | 4 | ± | + |
| 32 | 5 | 5 | 5 | 5 | 5 | 5 | 3 | 4 | ± | + |
| 33 | 5 | 5 | 5 | 5 | 5 | 5 | 4 | 5 | + | + |
| 34 | 5 | 5 | 5 | 5 | 5 | 5 | 4 | 4 | ± | ± |
| 35 | 5 | 5 | 5 | 5 | 5 | 5 | 3 | 4 | ± | ± |
| 36 | 5 | 5 | 5 | 5 | 5 | 5 | 4 | 4 | ± | + |
| 37 | 5 | 5 | 5 | 5 | 5 | 5 | 5 | 4 | ± | + |
| 38 | 5 | 5 | 5 | 5 | 5 | 5 | 4 | 4 | + | ± |
| 39 | 5 | 5 | 5 | 5 | 5 | 5 | 4 | 4 | ± | ± |
| 40 | 5 | 5 | 5 | 5 | 5 | 5 | 4 | 4 | ± | + |
| 41 | 3 | 5 | 5 | 5 | 2 | 5 | 3 | 3 | − | − |
| 42 | 5 | 5 | 5 | 5 | 2 | 5 | 3 | 4 | − | ± |
| 43 | 3 | 5 | 5 | 5 | 2 | 5 | 2 | 2 | − | − |
| 44 | 5 | 5 | 5 | 5 | 5 | 5 | 2 | 3 | − | ± |
| 45 | 5 | 5 | 5 | 5 | 4 | 5 | 3 | 3 | − | ± |
| 46 | 3 | 5 | 5 | 5 | 2 | 3 | 2 | 2 | − | − |
| 47 | 5 | 5 | 5 | 5 | 2 | 5 | 2 | 3 | − | − |
| 48 | 5 | 5 | 5 | 5 | 5 | 5 | 3 | 3 | − | ± |
| 49 | 5 | 5 | 5 | 5 | 4 | 3 | 3 | 3 | − | ± |
| 50 | 5 | 5 | 5 | 5 | 5 | 5 | 4 | 4 | ± | + |
| 51 | 5 | 5 | 5 | 5 | 5 | 5 | 3 | 4 | − | ± |
| 52 | 5 | 5 | 5 | 5 | 3 | 5 | 2 | 3 | ± | + |
| 53 | 5 | 5 | 5 | 5 | 5 | 5 | 4 | 4 | + | ++ |

TABLE 9

| Compound No. | Echinochlöa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 1 | 5 | 5 | 5 | 5 | 5 | 5 | 5 | — |
| 2 | 5 | 5 | 5 | 5 | 5 | 5 | 5 | — |
| 3 | 5 | 5 | 5 | 5 | 5 | 5 | 5 | — |
| 4 | 5 | 5 | 5 | 5 | 5 | 5 | 5 | — |
| 5 | 5 | 5 | 5 | 5 | 5 | 5 | 5 | — |
| 6 | 5 | 5 | 5 | 5 | 5 | 5 | 5 | — |
| 7 | 5 | 5 | 5 | 5 | 5 | 5 | 5 | — |
| 8 | 5 | 4 | 5 | 5 | 4 | 5 | 5 | — |
| 9 | 5 | 3 | 5 | 5 | 5 | 4 | 5 | — |
| 10 | 5 | 5 | 5 | 5 | 5 | 5 | 5 | — |
| 11 | 5 | 4 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 5 | 5 | 5 | 5 | 5 | 5 | — |
| 15 | 5 | 5 | 5 | 5 | 5 | 5 | 5 | — |
| 16 | 5 | 5 | 5 | 5 | 5 | 5 | 5 | — |
| 17 | 5 | 5 | 5 | 5 | 5 | 5 | 5 | — |
| 18 | 5 | 5 | 5 | 5 | 5 | 5 | 5 | — |
| 19 | 5 | 5 | 5 | 5 | 5 | 5 | 5 | — |
| 20 | 5 | 5 | 5 | 5 | 5 | 5 | 5 | — |
| 21 | 5 | 5 | 5 | 5 | 5 | 5 | 5 | — |
| 22 | 5 | 5 | 5 | 5 | 5 | 5 | 5 | — |
| 23 | 5 | 5 | 5 | 5 | 5 | 5 | 5 | — |
| 24 | 5 | 5 | 5 | 5 | 5 | 5 | 5 | — |
| 25 | 5 | 5 | 5 | 5 | 5 | 5 | 5 | — |
| 26 | 5 | 5 | 5 | 5 | 5 | 5 | 5 | — |
| 27 | 5 | 5 | 5 | 5 | 5 | 5 | 5 | — |
| 28 | 5 | 5 | 5 | 5 | 5 | 5 | 5 | — |
| 29 | 5 | 5 | 5 | 5 | 5 | 5 | 5 | — |
| 30 | 5 | 4 | 5 | 5 | 5 | 5 | 4 | — |
| 31 | 5 | 5 | 5 | 5 | 5 | 5 | 5 | — |
| 32 | 5 | 5 | 5 | 5 | 5 | 5 | 5 | — |
| 33 | 5 | 5 | 5 | 5 | 5 | 5 | 5 | — |
| 34 | 5 | 5 | 5 | 5 | 5 | 5 | 5 | — |
| 35 | 5 | 5 | 5 | 5 | 5 | 5 | 5 | — |
| 36 | 5 | 5 | 5 | 5 | 5 | 5 | 5 | — |
| 37 | 5 | 5 | 5 | 5 | 5 | 5 | 5 | — |
| 38 | 5 | 5 | 5 | 5 | 5 | 5 | 5 | — |
| 39 | 5 | 5 | 5 | 5 | 5 | 5 | 5 | — |
| 40 | 5 | 5 | 5 | 5 | 5 | 5 | 5 | — |
| 41 | 5 | 4 | 5 | 5 | 5 | 5 | 5 | — |
| 42 | 5 | 5 | 5 | .5 | 5 | 5 | 5 | — |
| 43 | 5 | 3 | 4 | 5 | 5 | 4 | 4 | — |
| 44 | 5 | 5 | 5 | 5 | 5 | 5 | 5 | — |
| 45 | 5 | 5 | 5 | 5 | 5 | 5 | 5 | — |
| 46 | 4 | 3 | 3 | 4 | 4 | 3 | 3 | — |
| 47 | 5 | 4 | 5 | 5 | 5 | 5 | 5 | — |
| 48 | 5 | 5 | 5 | 5 | 5 | 5 | 5 | — |
| 49 | 5 | 4 | 5 | 5 | 5 | 5 | 5 | — |
| 50 | 5 | 5 | 5 | 5 | 5 | 5 | 5 | — |
| 51 | 5 | 5 | 5 | 5 | 5 | 5 | 5 | — |
| 52 | 5 | 5 | 5 | 5 | 5 | 5 | 5 | — |
| 53 | 5 | 5 | 5 | 5 | 5 | 5 | 5 | — |

What is claimed is:

1. A derivative of 4,5-dihydro-1H-1,2,4-triazole-3-carboxamide represented by the formula (I):

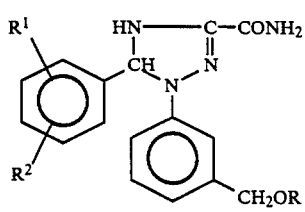

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s).

2. A derivative of 4,5-dihydro-1H-1,2,4-triazole-3-carboxamide according to claim 1, wherein R is a straight-chain alkyl group of 3 to 8 carbon atoms; a branched-chain alkyl group of 3 to 8 carbon atom; a cycloalkyl group of 4 to 7 carbon atoms; a (cycloalkyl)alkyl group of 4 to 8 carbon atoms; an alkenyl group of 3 to 6 carbon atoms; an alkynyl group of 3 to 6 carbon atoms; an alkyl group of 2 to 4 carbon atoms having an alkoxy group of 1 to 4 carbon atoms; a phenyl group; an aralkyl group of 7 to 9 carbon atoms; a phenyl group substituted by 1 to 3 halogen atoms or an alkyl group of from 2 to 7 carbon atoms substituted by 1 to 15 fluorine atoms.

3. A derivative of 4,5-dihydro-1H-1,2,4-triazole-3-carboxamide according to claim 2, wherein said derivative is 4,5-dihydro-1-[3-[(3-methylbutoxy)methyl]phenyl]-5-phenyl-1H-1,2,4-triazole-3-carboxamide.

4. A derivative of 4,5-dihydro-1H-1,2,4-triazole-3-carboxamide according to claim 2, wherein said derivative is 4,5-dihydro-1-[3-[(2,2-dimethylpropoxy)methyl]phenyl]-5-phenyl-1H-1,2,4-triazole-3-carboxamide.

5. A derivative of 4,5-dihydro-1H-1,2,4-triazole-3-carboxamide according to claim 2, wherein said derivative is 1-[3-[(cyclohexyl methyl)methyl]phenyl]-4,5-dihydro-5-phenyl-1H-1,2,4-triazole-3-carboxamide.

6. A derivative of 4,5-dihydro-1H-1,2,4-triazole-3-carboxamide according to claim 2, wherein said derivative is 1-[3-[2,2,2-trifluoroethoxy)methyl]phenyl]-4,5-dihydro-5-phenyl-1H-1,2,4-triazole-3-carboxamide.

7. A derivative of 4,5-dihydro-1H-1,2,4-triazole-3-carboxamide according to claim 2, wherein said derivative is 1-[3-[2,2,3,3-tetrafluoropropoxy)methyl]phenyl]-4,5-dihydro-5-phenyl-1H-1,2,4-triazole-3-carboxamide.

8. A derivative of 4,5-dihydro-1H-1,2,4-triazole-3-carboxamide according to claim 2, wherein said derivative is 1-[3-[(2,2,3,3,3-pentafluoropropoxy)methyl]phenyl]-4,5-dihydro-5-phenyl-1H-1,2,4-triazole-3-carboxamide.

9. A derivative of 4,5-dihydro-1H-1,2,4-triazole-3-carboxamide according to claim 2, wherein said derivative is 1-[3-[(2,2,3,4,4-hexafluorobutoxy)methyl]phenyl]-4,5-dihydro-5-phenyl-1H-1,2,4-triazole-3-carboxamide.

10. A derivative of 4,5-dihydro-1H-1,2,4-triazole-3-carboxamide according to claim 2, wherein said derivative is 1-[3-[(2,2,3,3,4,4,4-heptafluorobutoxy)methyl]phenyl]-4,5-dihydro-5-phenyl-1H-1,2,4-triazole-3-carboxamide.

11. A derivative of 4,5-dihydro-1H-1,2,4-triazole-3-carboxamide according to claim 2, wherein said derivative is 1-[3-[(2,2,3,3,4,4,5,5-octafluoropentyloxy)methyl]phenyl]-4,5-dihydro-5-phenyl-1H-1,2,4-triazole-3-carboxamide.

12. A derivative of 4,5-dihydro-1H-1,2,4-triazole-3-carboxamide according to claim 2, wherein said derivative is 1-[3-(2,2,3,3,4,4,5,5,6,6,7,7-dodecafluoroheptyloxy)-methyl]phenyl]-4,5-dihydro-5-phenyl-1,2,4-triazole-3-carboxamide.

13. A derivative of 4,5-dihydro-1H-1,2,4-triazole-3-carboxamide according to claim 2, wherein said derivative is 5-(2-fluorophenyl)-4,5-dihydro-1-[3-[(3-methylbutoxy)methyl]phenyl]-1H-1,2,4-triazole-3-carboxamide.

14. A derivative of 4,5-dihydro-1H-1,2,4-triazole-3-carboxamide according to claim 2, wherein said derivative is 5-(2-fluorophenyl)-4,5-dihydro-1-[3-[(2,2-dimethylpropoxy)methyl]phenyl]-1H-1,2,4-triazole-3-carboxamide.

15. A derivative of 4,5-dihydro-1H-1,2,4-triazole-3-carboxamide according to claim 2, wherein said derivative is 5-(2-fluorophenyl)-1-[3-[(hexyloxy)methyl]phenyl]-4,5-dihydro-1H-1,2,4-triazole-3-carboxamide.

16. A derivative of 4,5-dihydro-1H-1,2,4-triazole-3-carboxamide according to claim 2, wherein said derivative is 1-[3-[(cyclohexylmethoxy)methyl]phenyl]-5-(2-fluorophenyl)-4,5-dihydro-1H-1,2,4-triazole-3-carboxamide.

17. A derivative of 4,5-dihydro-1H-1,2,4-triazole-3-carboxamide according to claim 2, wherein said derivative is 1-[3-[(2,2,2-trifluoroethoxy)methyl]phenyl]-5-(2-fluorophenyl)-4,5-dihydro-1H-1,2,4-triazole-3-carboxamide.

18. A derivative of 4,5-dihydro-1H-1,2,4-triazole-3-carboxamide according to claim 2, wherein said derivative is 5-(2-fluorophenyl)-1-[3-[(2,2,3,3-tetrafluoropropoxy)methyl]phenyl]-4,5-dihydro-1H-1,2,4-triazole-3-carboximide.

19. A derivative of 4,5-dihydro-1H-1,2,4-triazole-3-carboxamide according to claim 2, wherein said derivative is 5-(2-fluorophenyl)-1-[3-[(2,2,3,3,3-pentafluoropropoxy)methyl]phenyl]-4,5-dihydro-1H-1,2,4-triazole-3-carboxamide.

20. A derivative of 4,5-dihydro-1H-1,2,4-triazole-3-carboxamide according to claim 2, wherein said derivative is 1-[3-[(2,2,3,4,4,4-hexafluorobutoxy)methyl]phenyl]-5-(2-fluorophenyl)-4,5-dihydro-1H-1,2,4-triazole-3-carboxamide.

21. A derivative of 4,5-dihydro-1H-1,2,4-triazole-3-carboxamide according to claim 2, wherein said derivative is 1-[3-[(2,2,3,3,4,4,4-heptafluorobutoxy)methyl]phenyl]-5-(2-fluorophenyl)-4,5-dihydro-1H-1,2,4-triazole-3-carboxamide.

22. A derivative of 4,5-dihydro-1H-1,2,4-triazole-3-carboxamide according to claim 2, wherein said derivative is 1-[3-[(2,2,3,3,4,4,5,5-octafluoropentyloxy)methyl]phenyl]-5-(2-fluorophenyl)-4,5-dihydro-1H-1,2,4-triazole-3-carboxamide.

23. A derivative of 4,5-dihydro-1H-1,2,4-triazole-3-carboxamide according to claim 2, wherein said derivative is 1-[3-[(2,2,3,3,4,4,5,5,6,6,7,7-dodecafluoroheptyloxy)methyl]phenyl]-5-(2-fluorophenyl)-4,5-dihydro-1H-1,2,4-triazole-3-carboxamide.

24. A derivative of 4,5-dihydro-1H-1,2,4-triazole-3-carboxamide according to claim 2, wherein said derivative is 1-[3-[(2,2,3,3,3-pentafluoropropoxy)methyl]phenyl]-5-(2,6-difluorophenyl)-4,5-dihydro-1H-1,2,4-triazole-3-carboxamide.

25. A herbicidal composition comprising a herbicidally effective amount of a derivative of 4,5-dihydro-1H-1,2,4-triazole-3-carboxamide represented by the formula (I):

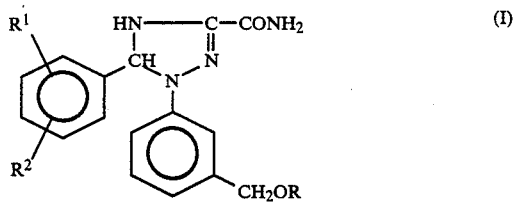

wherein $R^1$ represents a hydrogen atom, a halogen atom, an alkyl group of 1 to 3 carbon atoms or an alkoxy group of 1 to 3 carbon atoms, $R^2$ represents a hydrogen atom or a halogen atom and R represents a straight-chain alkyl group of 1 to 8 carbon atoms, a branched-chain alkyl group of 3 to 8 carbon atoms, a cycloalkyl group of 3 to 8 carbon atoms, a (cycloalkyl)alkyl group of 4 to 8 carbon atoms, an alkenyl group of 3 to 8 carbon atoms, an alkynyl group of 3 to 8 carbon atoms, an alkoxyalkyl group of 3 to 8 carbon atoms, a phenyl group, an aralkyl group of 7 to 9 carbon atoms, a phenyl group substituted by halogen atom(s) or an alkyl group of 2 to 8 carbon atoms which is substituted by fluorine atom(s) and a herbicidally acceptable carrier or an adjuvant.

* * * * *

UNITED STATES PATENT AND TRADEMARK OFFICE
CERTIFICATE OF CORRECTION

PATENT NO. : 4,897,106
DATED : January 30, 1990
INVENTOR(S) : Takafumi Shida, et al.

It is certified that error appears in the above-identified patent and that said Letters Patent is hereby corrected as shown below:

On the title page, after "[73] Assignee: Kureha Kagaku Kogyo Kabushiki Kaisha, Tokyo, Japan" insert --[*] Notice: The portion of the term of this patent subsequent to April 11, 2006 has been disclaimed.--

In claim 5, line 3, "cyclohexyl methyl)" should read --(cyclohexyl methoxy)--.

In claim 9, line 3, "(2,2,3,4,4 hexafluorobutoxy)" should read --(2,2,3,4,4,4-hexafluorobutoxy)--.

Signed and Sealed this

Fifth Day of May, 1992

Attest:

DOUGLAS B. COMER

Attesting Officer

Acting Commissioner of Patents and Trademarks